US006350612B1

(12) United States Patent
Rappuoli et al.

(10) Patent No.: US 6,350,612 B1
(45) Date of Patent: Feb. 26, 2002

(54) ISOLATION AND EXPRESSION OF DNA SEQUENCE ENCODING THE FIVE SUBUNITS OF *BORDETELLA PERTUSSIS* TOXIN

(75) Inventors: Rino Rappuoli, Quercegrossa-Monteriggioni; Alfredo Nicosia, Siena; Maria Beatrice Arico, Quercegrossa, all of (IT)

(73) Assignee: Chiron S.p.A., Siena (IT)

( * ) Notice: Subject to any disclaimer, the term of this patent is extended or adjusted under 35 U.S.C. 154(b) by 0 days.

(21) Appl. No.: 07/634,100

(22) Filed: Dec. 26, 1990

Related U.S. Application Data

(63) Continuation of application No. 07/006,438, filed on Jan. 23, 1987, now abandoned.

(30) Foreign Application Priority Data

| | | |
|---|---|---|
| Jan. 28, 1986 | (IT) | 19208/86 |
| Jul. 30, 1986 | (IT) | 21314/86 |

(51) Int. Cl.[7] .......................... C12N 15/83; C12N 1/12; C12N 15/09; C07H 21/04

(52) U.S. Cl. ................ 435/455; 435/252.1; 435/320.1; 536/23.7

(58) Field of Search ............................ 435/69.1, 252.1, 435/252.3, 252.33, 455, 320.1; 536/27, 23.7; 935/9, 27

*Primary Examiner*—Deborah Crouch
(74) *Attorney, Agent, or Firm*—Francis A. Paintin; Alisa A. Harbin; Robert P. Blackburn

(57) ABSTRACT

Cloning and sequencing of the Eco RI fragment of *B. pertussis* chromosomal DNA with 4696 base pairs, containing the genes which code for the five subunits of the pertussis toxin. A hybrid plasmid containing the DNA fragment or its further fragments and a micro-organism transformed by the hybrid plasmid and capable of expressing the cloned DNA fragment or further fragments thereof by synthesis of the pertussis toxin or one or more subunits of the pertussis toxin. The pertussis toxin or one or more subunits of the pertussis toxin so obtained are useful for the preparation of vaccines and diagnostic kits.

17 Claims, 23 Drawing Sheets

```
     1         10         20   25

S1   DDPPATVYRYDSRPPEDVFQNGFTAXG

S2   SQPGIVIPPQEQITQHGSPY

S3   VAPGIVIPPKALFTQQGGAYGXXXNG

S4   DVPYVLVKTNMVVTSVAMKPYEVTP
```

FIG. 2

```
     -40       -30       -20       -10      -1
S2                  MPIDRKTLCHLLSVLPLALLGSHVARA
S3                 MLINNKKLLHHILPILVLALLGMRTAQA
S1            MRCTRAIRQTARTGWLTWLAILAVTAPVTSPAWA
S4   MLRRFPTRTTAPGQGGARRSRVRALAWLLASGAMTHLSPALA
S5            MQRQAGLPLKANPMHTIASILLSVLGIYSPADVA
```

FIG. 4

10 30 50
GAATTCGTCGCCTCGCCCTGGTTCGCCGTCATGGCCCCCAAGGGAACCGACCCCAAGAT
ORF A 70 90 110
AATCGTCCTGCTCAACCGCCACATCAACGAGGCGCTGCAGTCCAAGGCGGTCGTCGAGGCC
130 150 170
TTTGCCGCCCAAGGCGCCACGCCGGTCATCGCCACGCCGGATCAGACCCGCGGCTTCAT
190 210 230
CGCAGACGAGATCCAGCGCTGGGCCGGCGTCGTGCGCGAAACCGGCGCCAAGCTGAAGTAG
250 270 290
CAGCGCAGCCCTCCAACGCGCCATCCCCGTCCGGCCGGCACCATCCCGCATACGTGTTG
310 330 350
GCAACCGCCAACGCGCATGCGTGCAGATTCGTCGTACAAAACCCTCGATTCTTCCGTACAT
370 390 410
CCCGCTACTGCAATCCAACACGGCATGAACGCTCCTTCGGCGCAAAGTCGCGCGATGGT
430 450 470
ACCGGTCACCGTCCGGACCGTGCTGACCCCCCTGCCATGGTGTGATCCGTAAAATAGGCAC
490 -35 510 530 -10
CATCAAAACGCAGAGGGGAAGACGGGATGCGTTGCACTCGGGCAATTCGCCAAACCGCA
MetArgCysThrArgAlaIleArgGlnThrAla
550 570
AGAACAGGCTGGCTGACGTGGCTGGCGATTCTTGCCGTCACGGCGCCCGTGACTTCGCCGG
ArgThrGlyTrpLeuThrTrpLeuAlaIleLeuAlaValThrAlaProValThrSerProA
610 630 650
CATGGGCCGACGATCCTCCCGCCACCGTATACCGCTATGACTCCCGCCCGCCGGAGGAC
laTrpAlaAspAspProProAlaThrValTyrArgTyrAspSerArgProProGluAsp
S1
670 690 710
GTTTTCCAGAACGGATTCACGGCGTGGGGAAACAACGACAATGTGCTCGACCATCTGACCG
ValPheGlnAsnGlyPheThrAlaTrpGlyAsnAsnAspAsnValLeuAspHisLeuThrG
750 770
GACGTTCCTGCCAGGTCGGCAGCAGCAACAGCGCTTTCGTCTCCACCAGCAGCAGCCGG
lyArgSerCysGlnValGlySerSerAsnSerAlaPheValSerThrSerSerSerArg
790 810 830
CGCTATACCGAGGTCTATCTCGAACATCGCATGCAGGAAGCGGTCGAGGCCGAACGCGCCG
ArgTyrThrGluValTyrLeuGluHisArgMetGlnGluAlaValGluAlaGluArgAlaG
850 870 890
GCAGGGGCACCGGCCACTTCATCGGCTACATCTACGAAGTCCGCGCCGACAACAATTTC
lyArgGlyThrGlyHisPheIleGlyTyrIleTyrGluValArgAlaAspAsnAsnPhe
910 930 950
TACGGCGCCGCCAGCTCGTACTTCGAATACGTCGACACTTATGGCGACAATGCCGGCCGTA
TyrGlyAlaAlaSerSerTyrPheGluTyrValAspThrTyrGlyAspAsnAlaGlyArgI
970 990 1010
TCCTCGCCGGCGCGCTGGCCACCTACCAGAGCGAATATCTGGCACACCGGCGCATTCCG
leLeuAlaGlyAlaLeuAlaThrTyrGlnSerGluTyrLeuAlaHisArgArgIlePro
1030 1050 1070
CCCGAAAACATCCGCAGGGTAACGCGGGTCTATCACAACGGCATCACCGGCGAGACCACGA
ProGluAsnIleArgArgValThrArgValTyrHisAsnGlyIleThrGlyGluThrThrT
1090 1110 1130
CCACGGAGTATTCCAACGCTCGCTACGTCAGCCAGCAGACTCGCGCCAATCCCAACCCC
hrThrGluTyrSerAsnAlaArgTyrValSerGlnGlnThrArgAlaAsnProAsnPro
1150 1170 1190
TACACATCGCGAAGGTCCGTAGCGTCGATCGTCGGCACATTGGTGCGCATGGCGCCGGTGA
TyrThrSerArgArgSerValAlaSerIleValGlyThrLeuValArgMetAlaProValI
1210 1230 1250
TAGGCGCTTGCATGGCGCGGCAGGCCGAAAGCTCCGAGGCCATGGCAGCCTGGTCCGAA
leGlyAlaCysMetAlaArgGlnAlaGluSerSerGluAlaMetAlaAlaTrpSerGlu
1270 1290 1310
CGCGCCGGCGAGGCGATGGTTCTCGTGTACTACGAAAGCATCGCGTATTCGTTCTAGACCT
ArgAlaGlyGluAlaMetValLeuValTyrTyrGluSerIleAlaTyrSerPheEnd

FIG. 3A-1

```
      1330                    1350                    1370
GGCCCAGCCCCGCCCAACTCCGGTAATTGAACAGCATGCCGATCGACCGCAAGACGCTC
                                  MetProIleAspArgLysThrLeu
      1390                    1410                    1430
TGCCATCTCCTGTCCGTTCTGCCGTTGGCCCTCCTCGGATCTCACGTGGCGCGGGCCTCCA
CysHisLeuLeuSerValLeuProLeuAlaLeuLeuGlySerHisValAlaArgAlaSerT
      1450                    1470                    1490      S2
CGCCAGGCATCGTCATTCCGCCGCAGGAACAGATTACCCAGCATGGCAGCCCCTATGGA
hrProGlyIleValIleProProGlnGluGlnIleThrGlnHisGlySerProTyrGly
      1510                    1530                    1550
CGCTGCGCGAACAAGACCCGTGCCCTGACCGTGGCGGAATTGCGCGGCAGCGGCGATCTGC
ArgCysAlaAsnLysThrArgAlaLeuThrValAlaGluLeuArgGlySerGlyAspLeuG
      1570                    1590                    1610
AGGAGTACCTGCGTCATGTGACGCGCGGCTGGTCAATATTTGCGCTCTACGATGGCACC
lnGluTyrLeuArgHisValThrArgGlyTrpSerIlePheAlaLeuTyrAspGlyThr
      1630                    1650                    1670
TATCTCGGCGGCGAATATGGCGGCGTGATCAAGGACGGAACACCCGGCGGCGCATTCGACC
TyrLeuGlyGlyGluTyrGlyGlyValIleLysAspGlyThrProGlyGlyAlaPheAspL
      1690                    1710                    1730
TGAAAACGACGTTCTGCATCATGACCACGCGCAATACGGGTCAACCCGCAACGGATCAC
euLysThrThrPheCysIleMetThrThrArgAsnThrGlyGlnProAlaThrAspHis
      1750                    1770                    1790
TACTACAGCAACGTCACCGCCACTCGCCTGCTCTCCAGCACCAACAGCAGGCTATGCGCGG
TyrTyrSerAsnValThrAlaThrArgLeuLeuSerSerThrAsnSerArgLeuCysAlaV
      1810                    1830                    1850
TCTTCGTCAGAAGCGGGCAACCGGTCATTGGCGCCTGCACCAGCCCGTATGACGGCAAG
alPheValArgSerGlyGlnProValIleGlyAlaCysThrSerProTyrAspGlyLys
      1870                    1890                    1910
TACTGGAGCATGTACAGCCGGCTGCGGAAAATGCTTTACCTGATCTACGTGGCCGGCATCT
TyrTrpSerMetTyrSerArgLeuArgLysMetLeuTyrLeuIleTyrValAlaGlyIleS
      1930                    1950                    1970
CCGTACGCGTCCATGTCAGCAAGGAAGAACAGTATTACGACTATGAGGACGCAACGTTC
erValArgValHisValSerLysGluGluGlnTyrTyrAspTyrGluAspAlaThrPhe
      1990                    2010                    2030
GAGACTTACGCCCTTACCGGCATCTCCATCTGCAATCCTGGATCATCCTTATGCTGAGACG
GluThrTyrAlaLeuThrGlyIleSerIleCysAsnProGlySerSerLeuCysEnd
                                                MetLeuArgAr
      2050                    2070                    2090
CTTCCCCACTCGAACCACCGCCCCGGGACAGGGCGGCGCCCGGCGGTCGCGCGTGCGCG
gPheProThrArgThrThrAlaProGlyGlnGlyGlyAlaArgArgSerArgValArgA
      2110                    2130                    2150
CCCTGGCGTGGTTGCTGGCATCCGGCGCGATGACGCATCTTTCCCCCGCCCTGGCCGACGT
laLeuAlaTrpLeuLeuAlaSerGlyAlaMetThrHisLeuSerProAlaLeuAlaAspVa
      2170                    2190                    2210      S4
TCCTTATGTGCTGGTGAAGACCAATATGGTGGTCACCAGCGTAGCCATGAAGCCGTATG
lProTyrValLeuValLysThrAsnMetValValThrSerValAlaMetLysProTyrG
      2230                    2250                    2270
AAGTCACCCCGACGCGCATGCTGGTCTGCGGCATCGCCGCCAAACTGGGCGCCGCGGCCAG
luValThrProThrArgMetLeuValCysGlyIleAlaAlaLysLeuGlyAlaAlaAlaSe
      2290                    2310                    2330
CAGCCCGGACGCGCACGTGCCGTTCTGCTTCGGCAAGGATCTCAAGCGTCCCGGCAGCA
rSerProAspAlaHisValProPheCysPheGlyLysAspLeuLysArgProGlySerS
      2350                    2370                    2390
GTCCCATGGAAGTCATGTTGCGCGCCGTCTTCATGCAACAACGGCCGCTGCGCATGTTTCT
erProMetGluValMetLeuArgAlaValPheMetGlnGlnArgProLeuArgMetPheLe
```

FIG. 3A-2

```
      2410                        2430                         2450
GGGTCCCAAGCAACTCACTTTCGAAGGCAAGCCCGCGCTCGAACTGATCCGGATGGTCG

       2470                        2490                        2510
AATGCAGCGGCAAGCAGGATTGCCCCTGAAGGCGAACCCCATGCATACCATCGCATCCATC
 MetGlnArgGlnAlaGlyLeuProLeuLysAlaAsnProMetHisThrIleAlaSerIle

uGlyProLysGlnLeuThrPheGluGlyLysProAlaLeuGluLeuIleArgMetValG
luCysSerGlyLysGlnAspCysProEnd
      2530                        2550                        2570
CTGTTGTCCGTGCTCGGCATATACAGCCCGGCTGACGTCGCCGGCTTGCCGACCCATCTG
LeuLeuSerValLeuGlyIleTyrSerProAlaAspValAlaGlyLeuProThrHisLeu
       2590                        2610        S5 2630
TACAAGAACTTCACTGTCCAGGAGCTGGCCTTGAAACTGAAGGGCAAGAATCAGGAGTTC
TyrLysAsnPheThrValGlnGluLeuAlaLeuLysLeuLysGlyLysAsnGlnGluPhe
      2650                        2670
TGCCTGACCGCCTTCATGTCGGGCAGAAGCCTGGTCCGGGCGTGCCTGTCCGACGCGGGA
CysLeuThrAlaPheMetSerGlyArgSerLeuValArgAlaCysLeuSerAspAlaGly
      2710                        2730                        2750
CACGAGCACGACACGTGGTTCGACACCATGCTTGGCTTTGCCATATCCGCGTATGCGCTC
HisGluHisAspThrTrpPheAspThrMetLeuGlyPheAlaIleSerAlaTyrAlaLeu
      2770                        2790                        2810
AAGAGCCGGATCGCGCTGACGGTGGAAGACTCGCCGTATCCGGGCACTCCCGGCGATCTG
LysSerArgIleAlaLeuThrValGluAspSerProTyrProGlyThrProGlyAspLeu
      2830                        2850                        2870
CTCGAACTGCAGATCTGCCCGCTCAACGGATATTGCGAATGAACCCTTCCGGAGGTTTCG
LeuGluLeuGlnIleCysProLeuAsnGlyTyrCysGluEnd
      2890                        2910                        2930
ACGTTTCCGCGCAATCCGCTTGAGACGATCTTCCGCCCTGGTTCCATTCCGGGAACACCG
      2950                        2970                        2990
CAACATGCTGATCAACAACAAGAAGCTGCTTCATCACATTCTGCCCATCCTGGTGCTCGC

     MetLeuIleAsnAsnLysLysLeuLeuHisHisIleLeuProIleLeuValLeuAl
      3010                        3030                        3050
CCTGCTGGGCATGCGCACGGCCCAGGCCCTTGCGCCAGGCATCGTCATCCCGCCGAAGGC
aLeuLeuGlyMetArgThrAlaGlnAlaValAlaProGlyIleValIleProProLysAl
                                 S3
      3070                        3090                        3110
ACTGTTCACCCAACAGGGCGGCGCCTATGGACGCTGCCCGAACGGAACCCGCGCCTTGAC
aLeuPheThrGlnGlnGlyGlyAlaTyrGlyArgCysProAsnGlyThrArgAlaLeuTh
      3130                                                    3170
CGTGGCCGAACTGCGCGGCAACGCCGAATTGCAGACGTATTTGCGCCAGATAACGCCCGG
rValAlaGluLeuArgGlyAsnAlaGluLeuGlnThrTyrLeuArgGlnIleThrProGl
      3190                        3210                        3230
CTGGTCCATATACGGTCTCTATGACGGTACGTACCTGGGCCAGGCGTACGGCGGCATCAT
yTrpSerIleTyrGlyLeuTyrAspGlyThrTyrLeuGlyGlnAlaTyrGlyGlyIleIl
      3250                        3270                        3290
CAAGGACGCGCCGCCAGGCGCGGGGTTCATTTATCGCGAAACTTTCTGCATCACGACCAT
eLysAspAlaProProGlyAlaGlyPheIleTyrArgGluThrPheCysIleThrThrIl
      3310                        3330                        3350
ATACAAGACCGGGCAACCGGCTGCGGATCACTACTACAGCAAGGTCACGGCCACGCGCCT
eTyrLysThrGlyGlnProAlaAlaAspHisTyrTyrSerLysValThrAlaThrArgLe
      3370                        3390                        3410
GCTCGCCAGCACCAACAGCAGGCTGTGCGCGGTATTCGTCAGGGACGGGCAATCGGTCAT
uLeuAlaSerThrAsnSerArgLeuCysAlaValPheValArgAspGlyGlnSerValIl
```

FIG. 3A-3

```
     3430                 3450                 3470
CGGAGCCTGCGCCAGCCCGTATGAAGGCAGGTACAGAGACATGTACGACGCGCTGCGGCG
eGlyAlaCysAlaSerProTyrGluGlyArgTyrArgAspMetTyrAspAlaLeuArgAr
     3490                 3510                 3530
CCTGCTGTACATGATCTATATGTCCGGCCTTGCCGTACGCGTCCACGTCAGCAAGGAAGA
gLeuLeuTyrMetIleTyrMetSerGlyLeuAlaValArgValHisValSerLysGluGl
     3550                 3570                 3590
GCAGTATTACGACTACGAGGACGCCACATTCCAGACCTATGCCCTCACCGGCATTTCCCT
uGlnTyrTyrAspTyrGluAspAlaThrPheGlnThrTyrAlaLeuThrGlyIleSerLe
                                               3650
CTGCAACCCGGCAGCGTCGATATGCTGAGCCGCCGGCTCGGATCTGTTCGCCTGTCCATG
uCysAsnProAlaAlaSerIleCysEnd
     3670                 3690                 3710
TTTTTCCTTGACGGATACCGCGAATGAATCCCTTGAAAGACTTGAGAGCATCGCTACCGC
                       ORF B
     3730                 3750                 3770
GCCTGGCCTTCATGGCAGCCTGCACCCTGTTGTCCGCCACGCTGCCCGACCTCGCCCAGG
     3790                                      3830
CCGGCGGCGGGCTGCAGCGCGTCAACCACTTCATGGCGAGCATCGTGGTCGTACTGCGCG
     3850                 3870                 3890
GCGCGTCAGTGGCCACGGTGACCATCGCCATAATCTGGGCGGGCTACAAGCTGCTGTTCC
     3910                 3930                 3950
GGCACGCCGATGTGCTGGACGTGGTGCGAGTGGTGCTGGCGGGACTGCTGATCGGCGCAT
     3970                 3990                 4010
CGGCCGAAATCGCTCGTTATCTGCTGACCTGAATCCTGGACGTATCGAACATGCGTGATC
                                                     ORF C
     4030                 4050                 4070
CGCTTTTCAAGGGCTGCACCCGGCCCGCGATGCTGATGGGCGTACCCGCCACGCCGCTGG
     4090                 4110
CCGTGTGCAGCGGCACCATTGCCCTGCTGGGCATCTGGTTCAGCATCGCCTTTCTGGCCT
     4150                 4170                 4190
TGTTTCCCGTGGCATTGCTGGCGATGCGGATCATGATCCGGCGCGATGACCAGCAGTTCC
     4210                 4230                 4250
GCCTGATCTGGCTTTACCTGCGCATGCGTTGGCTGAGCCGGGACCGCACGCATGCGTTCT
     4270                 4290                 4310
GGCAAAGTACCGTCTATGCGCCGCTGCGTTACGCCGAGCGCCgccGGCGCCTGCGcAAGC
     4330                 4350                 4370
CATGAACCGGCGCGGCGGCCAGACCGCATTTGCGGCCATTGCGCGCAACGAGCGCGCCAT
  ORF D
     4390                 4410                 4430
CGCTGCGTTCATCCCCTACAGCAGCCACCTGACGGACACGACGCTGATCACCCATGGCGC
                          4470                 4490
GGACCTGGTCCGCACCTGGCGCGTACAGGGGATCGCCTTCGAAAGCGCCGAGCCAGAGCT
     4510                 4530                 4550
GGTTTCGCAGCGCCATGAACAGCTCAACGGCCTGTGGCGCGCCATCTCGTGCGAGCAGGT
     4570                 4590                 4610
CGCGCTTTGGATCCATTGCATCCGGCGCAAGACGCAGGCCGGGTTGGATGCGCGGTACGA
     4630                 4650                 4670
AAATCCGTTCTGCCGCGCGCTCGACGCCTCGTACAACGCCCGGCTGAACGCGCGGCAGGC
     4690
AATGACGAACGAATTC
```

FIG. 3A-4

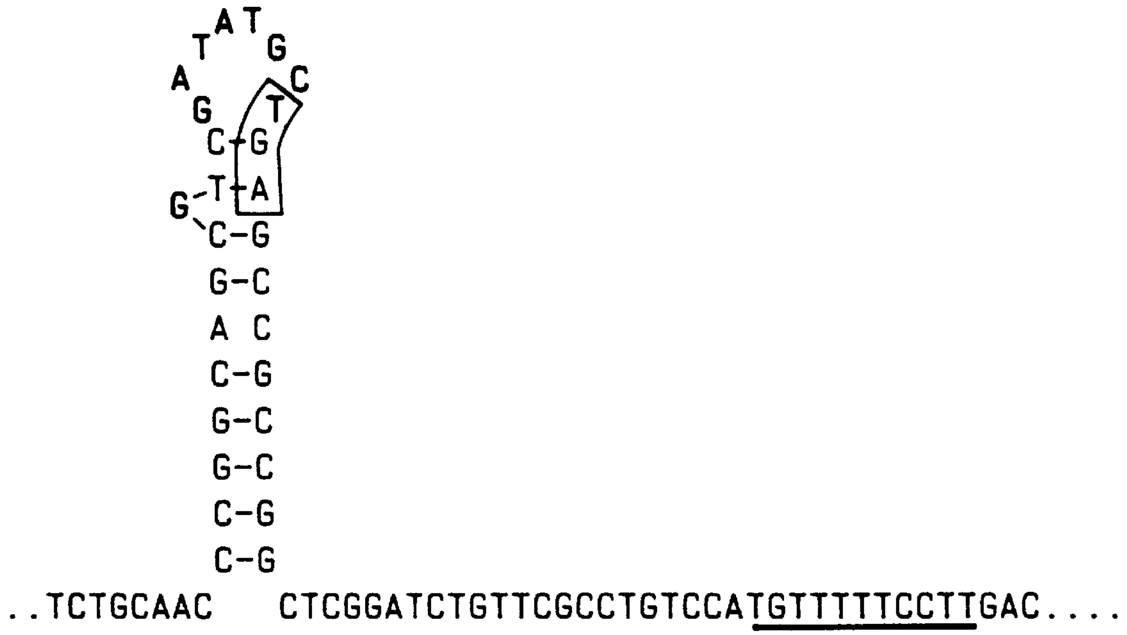

FIG. 5B

```
          -20          -10
S2   MPI.DRKTLCHLLSVLPLALLGSHVARASTPGIVIPPQEQITQHGSPYGR    22
     | |   | | | |  | |||||   | |  |||||||    || |  |||
S3   MLINNKKLLHHILPILVLALLGMRTAQAVAPGIVIPPKALFTQQGGAYGR    22

S2   CANKTRALTVAELRGSGDLQEYLRHVTRGWSIFALYDGTYLGGEYGGVIK    72
     | | |||||||||||   || |||  | ||||  ||||||||  ||| ||
S3   CPNGTRALTVAELRGNAELQTYLRQITPGWSIYGLYDGTYLGQAYGGIIK    72

S2   DGTPGGAFDLKTTFCIMTTRNTGQPATDHYYSNVTATRLLSSTNSRLCAV   122
     |  ||  |    |||| |   ||||| ||||| ||||||| |||||||||
S3   DAPPGAGFIYRETFCITTIYKTGQPAADHYYSKVTATRLLASTNSRLCAV   122

S2   FVRSGQPVIGACTSPYDGKYWSMYSRLRKMLYLIYVAGISVRVHVSKEEQ   172
     ||| || ||||| ||| | |  ||  ||  || ||  |  ||||||||||
S3   FVRDGQSVIGACASPYEGRYRDMYDALRRLLYMIYMSGLAVRVHVSKEEQ   172

S2   YYDYEDATFETYALTGISICNPGSSLC   199
     ||||||||| |||||||| |||  | |
S3   YYDYEDATFQTYALTGISLCNPAASIC   199
```

FIG. 6

```
     EcoR1           BamHI                    Pst1                         Bgl12 Xba1  Hind3
31A....G GGA ATT CGC GCG ACG GGA TCC GCG CAA CGT TGT TGC CAT TGC TGC AGC CGG AGA ACT GGT AGG TAT GGA AGA TCT CTA GAA GCT TGG C...
31B....CG GAA TTC GCG CGA CCC GAT CCG GGC AAC GTT GTT GCC ATT GCT GCA GGC GGA GAA CTC GTA GCT ATC GAA GAT CTC TAG AAG CTT GGC...
31C....GGG AAT TCG CGC GAC CGC ATC CGG GCA ACG TTG TTC CCA TTC CTC CAG GCG GAG AAC TGG TAG GTA TGG AAC ATC TCT AGA AGC TTG GC...
```

PTE211 (S2)

Fragment Sau96-Sma1 (1433-2064) cloned blunt in PEX31a/BamH1-blunt

```
        EcoR1              (BamH1-Sau96)
       _________           _____________
....gga att cgg gcg acc gga tcG GCC TCC ACG CCA......
....gly ile arg ala thr gly ser ALA SER THR PRO......
                                ---
```

PTE221 (S3)

Fragment SpH1-Dde1 (3014-3628) cloned blunt in PEX34c/BamH1-blunt

```
       EcoR1             (BamH1-Sph1)
      _________            _________
....gg aat tcg cgc gac cgg atc CGC ACG GCC CAG GCC GTT GCA CCA....
...... asn ser arg asp arg ile ARG THR ALA GLN ALA VAL ALA PRO....
                               --------------------
```

PTE240 (S4)

Fragment BstN1-BstN1 (2151-2600) cloned blunt in PEX31b/BamH1-blunt

```
        EcoR1             (BamH1-BstN1)
       ________           _____________
....g gaa ttc gcg cga ccg gat cTG GCC GAC GTT CCT....
......glu phe ala arg pro asp LEU ALA ASP VAL PRO....
                              -------
```

PTE230 (S5)

Fragment Aat2-SnaB1 (2558-3210) cloned blunt in PEX31a/BamH1-blunt

```
        EcoR1             (BamH1-Aat2)
       _________            ________
...g gga att cgc gcg acc gga tcC GCC GGC TTG CCG....
.....gly ile arg ala thr gly SER ALA GLY LEU PRO....
                             -------
```

FIG. 9

```
1     GAATTCGTCG CCTCGCCCTG GTTCGCCGTC ATGGCCCCCA AGGGAACCGA
51    CCCCAAGATA ATCGTCCTGC TCAACCGCCA CATCAACGAG GCGCTGCAGT
101   CCAAGGCGGT CGTCGAGGCC TTTGCCGCCC AAGGCGCCAC GCCGGTCATC
151   GCCACGCCGG ATCAGACCCG CGGCTTCATC GCAGACGAGA TCCAGCGCTG
201   GGCCGGCGTC GTGCGCGAAA CCGGCGCCAA GCTGAAGTAG CAGCGCAGCC
251   CTCCAACGCG CCATCCCCGT CCGGCCGGCA CCATCCCGCA TACGTGTTGG
                    T     C C  G     C      G
301   CAACCGCCAA CGCGCATGCG TGCAGATTCG TCGTACAAAA CCCTCGATTC
                    T     C G  G     C      G     A C
                          CGGAT
        C                 C         GC
351   TTCCGTACAT CCCGCTACTG CAATCCAACA CGGCATGAAC GCTCCTTCGG
        C                 T         GCA       C
                A                   A  T     C
401   CGCAAAGTCG CGCGATGGTA CCGGTCACCG TCCGGACCGT GCTGACCCCC
                A               G            C
        P             C      G   C G
451   CTGCCATGGT GTGATCCGTA AAATAGGCAC CATCAAAACG CAGAGGGGAA
                      C      G   CAG
501   GACGGGATGC GTTGCACTCG GGCAATTCGC CAAACCGCAA GAACAGGCTG
           A SI                                  G
551   GCTGACGTGG CTGGCGATTC TTGCCGTCAC GGCGCCCGTG ACTTCGCCGG
601   CATGGGCCGA CGATCCTCCC GCCACCGTAT ACCGCTATGA CTCCCGCCCG
                      G        G
651   CCGGAGGACG TTTTCCAGAA CGGATTCACG GCGTGGGGAA ACAACGACAA
               A
701   TGTGCTCGAC CATCTGACCG GACGTTCCTG CCAGGTCGGC AGCAGCAACA
             T A   C
751   GCGCTTTCGT CTCCACCAGC AGCAGCCGGC GCTATACCGA GGTCTATCTC
801   GAACATCGCA TGCAGGAAGC GGTCGAGGCC GAACGCGCCG GCAGGGGCAC
851   CGGCCACTTC ATCGGCTACA TCTACGAAGT CCGCGCCGAC AACAATTTCT
                                 A
901   ACGGCGCCGC CAGCTCGTAC TTCGAATACG TCGACACTTA TGGCGACAAT
951   GCCGGCCGTA TCCTCGCCGG CGCGCTGGCC ACCTACCAGA GCGAATATCT
1001  GGCACACCGG CGCATTCCGC CCGAAAACAT CCGCAGGGTA ACGCGGGTCT
         G                     G         C         C
                                                C
1051  ATCACAACGG CATCACCGGC GAGACCACGA CCACGGAGTA TTCCAACGCT
                                             A  C G   CT
```

FIG. 13A

```
1101  CGCTACGTCA GCCAGCAGAC TCGCGCCAAT CCCAACCCCT ACACATCGCG
                                       A           T

1151  AAGGTCCGTA GCGTCGATCG TCGGCACATT GGTGCGCATG GCGCCGGTGA
             ACC
      CG                                 C
1201  TAGGCGCTTG CATGGCGCGG CAGGCCGAAA GCTCCGAGGC CATGGCAGCC
      CG                                 C

1251  TGGTCCGAAC GCGCCGGCGA GGCGATGGTT CTCGTGTACT ACGAAAGCAT
              G    A

1301  CGCGTATTCG TTCTAGACCT GGCCCAGCCC CGCCCAACTC CGGTAATTCA
                                                          C

1351  ACAGCATGCC GATCGACCGC AAGACGCTCT GCCATCTCCT GTCCGTTCTG
                    AG
                     S2
1401  CCGTTGGCCC TCCTCGGATC TCACGTGGCG CGGGCCTCCA CGCCAGGCAT
               T          G          C
                                          C   G
1451  CGTCATTCCG CCGCAGGAAC AGATTACCCA GCATGGCAGC CCCTATGGAC
                                          C   G
1501  GCTGCGCGAA CAAGACCCGT GCCCTGACCG TGGCGGAATT GCGCGGCAGC
1551  GGCGATCTGC AGGAGTACCT GCGTCATGTG ACGCGCGGCT GGTCAATATT
1601  TGCGCTCTAC GATGGCACCT ATCTCGGCGG CGAATATGGC GGCGTGATCA
1651  AGGACGGAAC ACCCGGCGGC GCATTCGACC TGAAAACGAC GTTCTGCATC
                                        G         T
1701  ATGACCACGC GCAATACGGG TCAACCCGCA ACGGATCACT ACTACAGCAA
                     C

1751  CGTCACCGCC ACTCGCCTGC TCTCCAGCAC CAACAGCAGG CTATGCGCGG
1801  TCTTCGTCAG AAGCGGGCAA CCGGTCATTG GCGCCTGCAC CAGCCCGTAT
1851  GACGGCAAGT ACTGGAGCAT GTACAGCCGG CTGCGGAAAA TGCTTTACCT
                     A

1901  GATCTACGTG GCCGGCATCT CCGTACGCGT CCATGTCAGC AAGGAAGAAC
                    C  A
1951  AGTATTACGA CTATGAGGAC GCAACGTTCG AGACTTACGC CCTTACCGGC
                        G                              T
2001  ATCTCCATCT GCAATCCTGG ATCATCCTTA TGCTGAGACG CTTCCCCACT
                                         S4
                                         C   C
2051  CGAACCACCG CCCCGGGACA GGGCGGCGCC CGGCGGTCGC GCGTGCGCGC
                                 A       T        CA
2101  CCTGGCGTGG TTGCTGGCAT CCGGCGCGAT GACGCATCTT TCCCCCGCCC
      A          G
2151  TGGCCGACGT TCCTTATGTG CTGGTGAAGA CCAATATGGT GGTCACCAGC
```

FIG. 13B

```
2201 GTAGCCATGA AGCCGTATGA AGTCACCCCG ACGCGCATGC TGGTCTGCGG

                 G
2251 CATCGCCGCC AAACTGGGCG CCGCGGCCAG CAGCCCGGAC GCGCACGTGC
                 G

      T                               CT
2301 CGTTCTGCTT CGGCAAGGAT CTCAAGCGTC CCGGCAGCAG TCCCATGGAA

                                                     C
2351 GTCATGTTGC GCGCCGTCTT CATGCAACAA CGGCCGCTGC GCATGTTTCT
                                                     C

2401 GGGTCCCAAG CAACTCACTT TCGAAGGCAA GCCCGCGCTC GAACTGATCC

                G
2451 GGATGGTCGA ATGCAGCGGC AAGCAGGATT GCCCCTGAAG GCGAACCCCA
                ->S5
2501 TGCATACCAT CGCATCCATC CTGTTGTCCG TGCTCGGCAT ATACAGCCCG

        C             C                                 G
2551 GCTGACGTCG CCGGCTTGCC GACCCATCTG TACAAGAACT TCACTGTCCA
        C

            AA             A            C
2601 GGAGCTGGCC TTGAAACTGA AGGGCAAGAA TCAGGAGTTC TGCCTGACCG

              C A                                         A
2651 CCTTCATGTC GGGCAGAAGC CTGGTCCGGG CGTGCCTGTC CGACGCGGGA
              C

       G AC  G  G
2701 CACGAGCACG ACACGTGGTT CGACACCATG CTTGGCTTTG CCATATCCGC

                                                  A
2751 GTATGCGCTC AAGAGCCGGA TCGCGCTGAC GGTGGAAGAC TCGCCGTATC

2801 CGGGCACTCC CGGCGATCTG CTCGAACTGC AGATCTGCCC GCTCAACGGA

                     C    C  C  C      A       T  G      C
2851 TATTGCGAAT GAACCCTTCC GGAGGTTTCG ACGTTTCCGC GCAATCCGCT
                    T

          T
2901 TGAGACGATC TTCCGCCCTG GTTCCATTCC GGGAACACCG CAACATGCTG

                       C                          C
2951 ATCAACAACA AGAAGCTGCT TCATCACATT CTGCCCATCC TGGTGCTCGC
                                          ->S3

                         G              A
3001 CCTGCTGGGC ATGCGCACGG CCCAGGCCGT TGCGCCAGGC ATCGTCATCC

                C   C     A
3051 CGCCGAAGGC ACTGTTCACC CAACAGGGCG GCGCCTATGG ACGCTGCCCG

                             C  G                 CG
3101 AACGGAACCC GCGCCTTGAC CGTGGCCCAA CTGCGCGGCA ACGCCGAATT

                     A                                    G
3151 GCAGACGTAT TTGCGCCAGA TAACGCCCGG CTGGTCCATA TACGGTCTCT
```

FIG. 13C

```
                              T
3201 ATGACGGTAC GTACCTGGGC CAGGCGTACG GCGGCATCAT CAAGGACGCG
      GC  G C   GC CTC          AGA   C
3251 CCGCCAGGCG CGGGGTTCAT TTATCGCGAA ACTTTCTGCA TCACGACCAT
     C   T C      A  G     A A A
3301 ATACAAGACC GGGCAACCGG CTGCGGATCA CTACTACAGC AAGGTCACGG
     G
                   G                G               C    C
3351 CCACGCGCCT GCTCGCCAGC ACCAACAGCA GGCTGTGCGC GGTATTCGTC
          T  AA   C  C        C       A  C         C  A  TC
3401 AGGGACGGGC AATCGGTCAT CGGAGCCTGC GCCAGCCCGT ATGAAGGCAG
                              C
         G                 T           T            G
3451 GTACAGAGAC ATGTACGACG CGCTGCGGCG CCTGCTGTAC ATGATCTATA
                           T
            T                                    A
3501 TGTCCGGCCT TGCCGTACGC GTCCACGTCA GCAAGGAAGA GCAGTATTAC
          T  A         G    G                     T  C   A
3551 GACTACGAGG ACGCCACATT CCAGACCTAT GCCCTCACCG GCATTTCCCT
                  G  A  C           T     TC   C  C T
3601 CTGCAACCCG GCAGCGTCGA TATGCTGAGC CGCCGGCTCG GATCTGTTCG
       ACC G CA     CCA  C    A    TC  A      C  G
3651 CCTGTCCATG TTTTTCCTTG ACGGATACCG CGAATGAATC CCTTGAAAGA
         C
         G  A G C A GG                               T
3701 CTTGAGAGCA TCGCTACCGC GCCTGGCCTT CATGGCAGCC TGCACCCTGT
        C
       CTG                 T           GA        C     A
3751 TGTCCGCCAC GCTGCCCGAC CTCGCCCAGG CCGGCGGCGG GCTGCAGCGC
           AG              G     CAC    G            A  G
3801 GTCAACCACT TCATGGCGAG CATCGTGGTC GTACTGCGCG GCGCGTCAGT
              C             C  A      C
3851 GGCCACGGTG ACCATCGCCA TAATCTGGGC GGGCTACAAG CTGCTGTTCC
3901 GGCACGCCGA TGTGCTGGAC GTGGTGCGAG TGGTGCTGGC GGGACTGCTG
                              C
3951 ATCGGCGCAT CGGCCGAAAT CGCTCGTTAT CTGCTGACCT GAATCCTGGA
                    C                              T
4001 CGTATCGAAC ATGCGTGATC CGCTTTTCAA GGGCTGCACC CGGCCCGCGA
4051 TGCTGATGGG CGTACCCGCC ACGCCGCTGG CCGTGTGCAG CGGCACCATT
4101 GCCCTGCTGG GCATCTGGTT CAGCATCGCC TTTCTGGCCT TGTTTCCCGT
4151 GGCATTGCTG GCGATGCGGA TCATGATCCG GCGCGATGAC CAGCAGTTCC
```

FIG. 13D

```
4201  GCCTGATCTG GCTTTACCTG CGCATGCGTT GGCTGAGCCG GGACCGCACG
4251  CATGCGTTCT GGCAAAGTAC CGTCTATGCG CCGCTGCGTT ACGCCGAGCG
4301  CCGCCGGCGC CTGCGCAAGC CATGAACCGG CGCGGCGGCC AGACCGCATT
                             C
4351  TGCGGCCATT GCGCGCAACG AGCGCGCCAT CGCTGCGTTC ATCCCCTACA
4401  GCAGCCACCT GACGGACACG ACGCTGATCA CCCATGGCGC GGACCTGGTC
4451  CGCACCTGGC GCGTACAGGG GATCGCCTTC GAAAGCGCCG AGCCAGAGCT
4501  GGTTTCGCAG CGCCATGAAC AGCTCAACGG CCTGTGGCGC GCCATCTCGT
4551  GCGAGCAGGT CGCGCTTTGG ATCCATTGCA TCCGGCGCAA GACGCAGGCC
                 A
4601  GGGTTGGATG CGCGGTACGA AAATCCGTTC TGCCGCGCGC TCGACGCCTC
                                                   G
4651  GTACAAGGCC CGGCTGAACG CGCGGCAGGC AATGACGAAC GAATTCTACC
                                                   G
4701  TCACCCTGGT ATATCGGCCT GGCCACGCCG CGCTCGGCAA GCGTGCGCAT
4751  CACGGCCAGG CCGAGGTCCG CCGGCAACTG CTGGCCCATG TACGACGCAT
                                                           G
4801  GGACGAAATC GGATCCCTGA TCGAAACGAC GCTGCGCAGC CATGGCGAGA
4851  ACCACGAGCA GGCCATCACC GTGCTGGGCT GCGAGACGGA CAGCGCCGGC
4901  CGGCGATACT CCCGGACGCT GACCCTGCTC GAATTC
```

FIG. 13E

S1
```
  1  MRCTRAIRQT ARTGWLTWLA ILAVTAPVTS PAWADDPPAT VYRYDSRPPE
                R
                           E
 51  DVFQNGFTAW GNNDNVLDHL TGRSCQVGSS NSAFVSTSSS RRYTEVYLEH
                          E
101  RMQEAVEAER AGRGTGHFIG YIYEVRADNN FYGAASSYFE YVDTYGDNAG
                                    I
                                                         P
151  RILAGALATY QSEYLAHRRI PPENIRRVTR VYHNGITGET TTTEYSNARY
                                    T                    P L
                                              T          P
201  VSQQTRANPN PYTSRRSVAS IVGTLVRMAP VIGACMARQA ESSEAMAAWS
              T          T                    T          P
251  ERAGEAMVLV YYESIAYSF*
              T
```

S2
```
                                                         G
  1  MPIDRKTLCH LLSVLPLALL GSHVARASTP GIVIPPQEQI TQHGSPYGRC
              S           F    C                         G
 51  ANKTRALTVA ELRGSGDLQE YLRHVTRGWS IFALYDGTYL GGEYGGVIKD
                                   R  F
101  GTPGGAFDLK TTFCIMTTRN TGQPATDHYY SNVTATRLLS STNSRLCAVF
151  VRSGQPVIGA CTSPYDGKYW SMYSRLRKML YLIYVAGISV RVHVSKEEQY
                                    *
201  YDYEDATFET YALTGISICN PGSSLC*
```

FIG. 15A

```
S3                     L         R↓    S        L K
  1   MLINNKKLLH HILPILVLAL LGMRTAQAVA PGIVIPPKAL FTQQGGAYGR

           A        T                                S
 51   CPNGTRALTV AELRGNAELQ TYLRQITPGW SIYGLYDGTY LGQAYGGIIK

           R AGAL    QKP        Y    DT                     G
101   DAPPGAGFIY RETFCITTIY KTGQPAADHY YSKVTATRLL ASTNSRLCAV
                       M
           A   KPL     TR   QSS     G   V           V
151   FVRDGQSVIG ACASPYEGRY RDMYDALRRL LYMIYMSGLA VRVHVSKEEQ
                                V
              E            I
201   YYDYEDATFQ TYALTGISLC NPAASIC*

S4         L              P              T M H    Q↓
  1   MLRRFPTRTT APGQGGARRS RVRALAWLLA SGAMTHLSPA LADVPYVLVK

 51   TNMVVTSVAM KPYEVTPTRM LVCGIAAKLG AAASSPDAHV PFCFGKDLKR

         S
101   PGSSPMEVML RAVFMQQRPL RMFLGPKQLT FEGKPALELI RMVECSGKQD

151   CP*

S5    V                         ↓                           T
  1   MQRQAGLPLK ANPMHTIASI LLSVLGIYSP ADVAGLPTHL YKNFTVQELA

            D   L        P              E   RTRG
 51   LKLKGKNQEF CLTAFMSGRS LVRACLSDAG HEHDTWFDTM LGFAISAYAL
                       P
101   KSRIALTVED SPYPGTPGDL LELQICPLNG YCE*
```

FIG. 15B

ISOLATION AND EXPRESSION OF DNA SEQUENCE ENCODING THE FIVE SUBUNITS OF *BORDETELLA PERTUSSIS* TOXIN

This application is a continuation of Ser. No. 07/006,438 filed Jan. 23, 1987, which is now abandoned.

DESCRIPTION

The present invention relates to a cloned and sequenced ECO RI fragment of *Bordetella pertussis* chromosomal DNA containing the genes which code for the five subunits of the pertussis toxin, useful for the preparation of the pertussis toxin or of one or more subunits of the pertussis toxin.

The present invention also relates to a hybrid plasmid containing the cloned and sequenced DNA fragment or further fragments thereof and to a micro-organism transformed by the hybrid plasmid and capable of expressing the cloned DNA fragment or further fragments thereof by synthesis of the pertussis toxin or one or more subunits of the pertussis toxin.

The invention also concerns a method for the preparation of the pertussis toxin or one or more subunits of the pertussis toxin which includes the growth of the micro-organism transformed by the hybrid plasmid in a suitable culture medium.

The pertussis toxin or one or more subunits of the pertussis toxin thus obtained is useful for the preparation of vaccines and diagnostic kits.

Pertussis is an infection of the respiratory tract caused by *Bordetella pertussis* (*B. pertussis*), a Gram-negative coccobacillus which is transmitted directly through the air during a catarrhal or conclusive period from the infirmed to a susceptible healthy individual.

Pertussis may cause respiratory complications, nerve damage and high mortality, particularly in children in low socio-economic groups and in new born babies without maternal, anti-pertussis antibodies. The clinical course of pertussis includes four phases: incubation, cattarhal phase, paroxysmic phase, and a convalescent phase.

During the first two phases there are symptoms comparable to those of a common cold and the *B. pertussis* may be isolated easily from the patients.

During the paroxysmic phase, characterised by the symptoms of pertussis itself, the bacterium is isolated only in 50% of cases.

During the convalescent phase it is no longer possible to isolate *B. pertussis* from the nasopharynx although the patients still have symptoms of pertussis.

It is clear from this that the more violent clinical indications of the illness occur after the disappearance of the bacteria and from this it may be inferred that pertussis is not due to invasion of the respiratory tract by the bacterial but to a toxic state induced by the bacteria but which remains even after their disappearance.

The charge of *B. pertussis* from phase I (virulent) to phase III (non-virulent is accomplished by a loss of capacity to synthesize certain substances such as: the pertussis toxin (PT), haemolysin (hly), adenylcyclase (Adc) and the dermonecrotic toxin (Dmt).

Tests carried out be Munoz. J. J. et al. (1981) (Inf. Immun. 32. 243) have shown that a vaccine constituted by the pertussis toxin alone, suitably detoxified with glutaraldehyde, is capable of protecting mice from death due to the intracerebral administration of bacteria in phase I.

Recent studies (Weiss, A. A. et al. (1983) Inf. Immun 42, 33; Weiss, A. A. et al (1984) J. Inf. Dis. 150, 219) have shown that not all these five substances contribute with equal effect to the virulence of *B. pertussis*. Weiss has succeeded in isolating the mutants which have lost selectively only one of the factors of the virulence by the insertion of a transposable element, a transposon (Tn5), into the genome of *B. pertussis*. From tests carried out in animals, it was found that only the mutants which had lost their capacity to synthesize PT or Adc had, at the same time, lost their virulence.

Hence the pertussis toxin (PT) is the major factor in the virulence of *Bordetella pertussis.*

The pertussis toxin a protein with a molecular weight of about 100,000 dalton, is produced and released into the extra cellular environment by *Bordetella pertussis* during phase I.

PT has an enzymatic activity and deactivates ADP-ribosilandol, a GTP-dependent protein which is involved in the deactivation of cellular adenylcylase.

Like other toxins, the pertussis toxin is also constituted by two different fragments: A and B.

The A fragment, which is toxic, comprises a single polypeptide S1 (subunit S1) having a molecular weight of about 28,000 daltons, which can bind an ADP-ribose group to a GTP-binding protein G, which inhibits adenylate cyclase involved in the transmission of signals from the outside to the inside of cells.

The B fragment comprises five polypeptides S2, S3, S4 and S5 (subunits S2, S3, S4, S5) with molecular weights of 23,000, 22,000, 12,000 and 9,000 daltons respectively, disposed as two dimers S2+S4 and S3+S4 and a monomer S5.

The B fragment binds to measure receptors of eucaryotic cells facilitating entry of S1 into the cells.

At present a pertussis vaccine is used which, although giving permanent immunity, has numerous disadvantages.

The vaccine is in fact constituted by virulent bacteria (phase I) treated at 56° C. for 30 minutes to remove a toxin which is heat-labile (dermonecrotic toxin) and killed by merthiolate.

Since the bacteria are not subjected to any detoxification treatment, any toxic substance which withstands 56° C. for 30 minutes is included in the vaccine.

The presence of such toxic substances, particularly from the PT, causes side effects which vary from simple flushing to permanent neurological damage and/or death.

All this has meant that over the last ten years the use of the vaccine has been reduced drastically with a consequent re-explosion of cases of pertussis.

Recently a vaccine has been prepared which is constituted essentially by fibrous haemagglutinin (FHA) and pertussis toxin detoxified with formaldehyde (Sato Y., et al: Lancet Jan. 21. 122 (1984)).

However, this vaccine has disadvantages such as: the presence of side effects, even though less than those of the conventional vaccine; obtaining a product which is too crude to be used such; and the extreme variability of the product from preparation to preparation.

There is thus a need to provide an effective vaccine which can be produced on a large scale and which does not have the disadvantages noted above.

Thus, for example, recent developments in the biochemical filed and in the field of genetic engineering have made it possible to prepare synthetic vaccines and micro-organisms capable of producing proteins useful for the preparation of vaccines with high yields.

In every case a key element for the preparation of the vaccines is a knowledge of the amino acid sequence of the protein and the nucleotide sequence of the gene and/or genes which code for the protein.

Once the gene which codes for a certain protein has been cloned and its nucleotide and amino acid sequences have been determined, the production of these on a large scale and the construction of synthetic vaccines is possible with current techniques.

At present nothing is known of the nature, structure and expression of the gene and/or genes of the pertussis toxin and no data other than the amino acid composition of the individual subunits of the pertussis toxin is available.

Accordingly, by the present invention there has been determined the aminoterminal amino acid sequence of the subunits S1, S2, S3 and S4 of the pertussis toxin and an Eco-RI-fragment of *Bordetella pertussis* chromosomal DNA has been cloned and sequenced, the fragment having 4696 base pairs and containing the genes which code for the five subunits of the pertussis toxin, useful for the preparation of the pertussis toxin or of one or more subunits of the pertussis toxin. Thus a subject of the present invention is a cloned and sequenced 4696-base-pair Eco RI fragment of *Bordetella pertussis* chromosomal DNA containing the genes which code for the five subunits of the pertussis toxin or fragments thereof, useful for the production of the pertussis toxin or of one or more subunits of the pertussis toxin.

Another subject of the invention is a hybrid plasmid containing the cloned and sequenced DNA fragment or further fragments thereof.

A further subject of the present invention is a micro-organism transformed by the hybrid plasmid and capable of expressing the cloned DNA fragment or its further fragments by synthesis of the pertussis toxin or of one or more subunits of the pertussis toxin.

Another subject of the present invention is a method for

Another subject of the present invention is a method for the preparation of the pertussis toxin or of one or more subunits of the pertussis toxin by growth of the transformed micro-organism.

A further subject of the present invention is the use of the pertussis toxin or of one or more subunits of the pertussis toxin for the preparation of anti-pertussis vaccines and diagnostic kits.

Yet another subject of the invention is the protein of the pertussis toxin in which the subunits S1, S2, S3, S4 have the amino acid sequences given in FIGS. 2 and 3. Further subjects of the present invention will become apparent from the description and the experimental examples which follow.

BRIEF DESCRIPTION OF THE TERMS USED IN THE DESCRIPTION

Genetic Code: by this term is meant the relationship existing between the nucleotide sequence in DNA and the amino acid sequence in a protein.

An important characteristic of the genetic code is the fact that the synthesis of each amino acid is specified by a sequence of three nucleotides in the DNA, also called a triplet or condon.

The genetic code is universal, that is, a particular triplet codes the same amino acid in all living beings.

Reading phase or frame: by this term is meant a group of triplets used by a cell to decode the genetic message.

Cloning vectors: these are molecules of DNA which contain all the genetic information to enable them to replicate when transferred into a host micro-organism.

Examples of cloning vectors commonly used in genetic engineering are the plasmids and the DNA of several bacteriophages.

The plasmid DNA, which is circular, may be cut by suitable techniques and a heterologous DNA fragment may be inserted and the ring reclosed to form a larger molecule containing the heterologous DNA, the so-called molecule of recombinant DNA or hybrid plasmid.

The DNA of bacteriophage may contain a segment of heterologous DNA inserted instead of several non-essential genes. Both these vectors are used for the insertion of heterologous DNA fragments and for the subsequent transformation of micro-organisms, also called host cells.

Restriction enzymes: these are hydrolytic enzymes capable of cutting a DNA molecule at specific sites, so-called recognition sites for the restriction enzymes.

Transposons: these are segments of DNA which may transpose and insert themselves at different points in the genome and give rise to the process known as transposition.

Promoter: a specific region of the DNA molecule in which the RNA polymerase starts transcription.

The promoter includes a recognition site and a binding site for the enzyme.

Termination Region: a specific region of the DNA molecule in which transcription ends.

Translation: this is the passage of genetic information from the mRNA to the protein according to the rules of the genetic code.

Expression: this term means the mechanism by means of which an organism can synthesise a protein coded by a specific gene.

In this case one says that the gene is expressed by the micro-organism.

In general, a method for obtaining a heterologous protein by recombinant DNA techniques requires the cloning of the gene which codes for the protein, where by cloning is meant the sequencing, isolation and purification of the gene and/or genes which code for the protein. Once cloned, the gene may be inserted in an expression vector and the molecule of recombinant DNA thus obtained may then be introduced into a host micro-organism where the gene will replicate simultaneously with the replication of the micro-organism, from which it may be re-isolated by conventional methods.

With this method of operation it is possible to provide a continuously renewable source of the gene which can then be manipulated further, modified and inserted in other vectors or in different sites in the same vector.

The transformed micro-organism, grown in a suitable culture medium, will enable the protein coded by the gene to be synthesized.

Accordingly by the present invention there has been cloned and sequenced an Eco RI fragment of *Bordetella pertussis* BP 165 chromosomal DNA containing the genes which code for the five subunits of the pertussis toxin and the aminoterminal sequence of the subunits S1, S2, S3 and S4 of the pertussis toxin has been determined. In particular, the pertussis toxin produced by *Bordetella pertussis* 165 has been purified by affinity chromatography and the subunits subsequently separated by electrophoresis in polyacrylamide sodium dodecylsulphate gels as shown in FIG. 1.

The individual subunits were then separated and purified by electroelution (Hunkapiller M. W. et al.; Methods in Enzymology 91, 227–236, 1983) and analysed in a gas-phase microsequencer.

The aminoterminal sequence of the subunits S1, S2, S3 and S4 is given in FIG. 2.

A gene library was then constructed with the use of the *E. Coli* lambda phage EMBL4 (bought from Promega Biotec 280 S. Fish Hatchery Road, Madison, Wis. 53711 USA) starting from the strain *Bordetella pertussis* BP356.

This strain is a mutant which does not produce an active toxin and has a single transposon TN5 inserted into its chromosome [Weiss, A. A. et al. Infect. Immun. 42, 33–41 (1983)].

The chromosomal DNA of the said strain was separated from the cells and, after purification, was partially digested with the restriction enzyme Sau3A1 by the method and under the operative conditions described by Maniatis T. et al.: Molecular Cloning a Laboratory Manual Cold Spring Harbor N.Y., (1982). The fragments of chromosomal DNA with 15000 to 20000 base pairs were then separated and cloned in the *E. coli* lambda phage vector EMBL4 previously prepared as reported by Frischauf A. et al. [J. Mol. Biol. 170, 827–842 (1983)] with the use of the Promega Biotec "Packagene" Kit according to the method described by Maniatis T. et al. (Molecular Cloning a Laboratory Manual Cold Spring Harbor N.Y. 1982).

The recombinant phages were then used to transform *E. coli* NNM 539 cells Promega Biotec).

The phages containing DNA fragments in which the transposon TN5 had been inserted were then selected from the transformed cells by the plate-hybridization technique with a radio-active probe for the TN5 DNA.

The recombinant phage DNA was then extracted from the positive recombinant phages and, after digestion with the restriction enzyme Eco-RI, the DNA fragments containing the transposon TN5 were separated and selected by hybridization with a probe for TN5 DNA.

In this manner it was possible to isolate an Eco-RI DNA fragment with about 10500 base pairs containing the entire sequence of the transposon TN5 flanked on the one hand by about 1100 base pairs and on the other by about 3500 base pairs of chromosomal DNA of *Bordetella pertussis* BP 356.

The Eco-RI fragments with 10500 base pairs were then digested with the restriction enzyme Hinc II and the DNA fragments containing the junction between the TN5 and the chromosomal DNA were isolated by hybridization with a probe for TN5 DNA.

Two fragments were thus identified, one with about 500 base pairs and the other with 1900 base pairs.

The two fragments, purified by electroelution, were then cloned in the phage vector M13mp8 (New England Biolabs) the DNA thereof had previously been cut but the restriction enzyme Hinc II.

The nucleotide sequences of the two fragments were then determined, starting from the Hinc II site according to the technique described by Sanger F. S.: Proc. Natl. Acad. Sci. 74, 5463 (1977).

The fragment with 1900 base pairs had at about 400 nucleotides from the Hinc II site, a nucleotide sequence (FIG. 3A from 3030 to 3100 bp) which, translated into the corresponding amino acids according to the genetic code, corresponded exactly to the amino acid sequence determined previously for the subunit S3 and given in FIG. 2.

This result confirms that the cloned DNA fragment with 10500 base pairs contained the gene for the pertussis toxin.

The fragment with 1900 bp was then used as a hybridization probe to identify and isolate a fragment DNA fragment containing the gene for and/or which codes for the pertussis toxin from the chromosomal DNA of *B. pertussis* EP 165 for which a gene library had been constructed as described above for *B. pertussis* BP 356.

At the end of the cloning operations, a 4696 base-pair Eco RI fragment of chromosomal DNA was isolated which we knew contained at least the gene which codes for the subunit S3 in that the fragment hybridized with the specific probe for S3.

The said fragment or parts thereof were then cloned in the phage vector M13mp8 and M13mp9 and the recombinant phage DNA thus obtained was sequenced.

Analysis of the sequence has enabled various open reading frames (ORFS) to be identified.

A comparison of their coding properties and the aminoterminal sequences of the subunits of the toxin have shown that four of these ORFS in fact code for the subunits S1, S2, S3 and S4 of the pertussis toxin.

Moreover, the molecular weight, the amino acid composition and the electric charges were in exact accordance with published data (Table 1) A fifth ORFS was also identified, placed between those which code for S4 and S3, which codes for a protein with a molecular weight and an amino acid composition identical to those described for the subunit S5.

These five open reading frames are grouped in a fragment, with 3200 base pairs in the following order: S1, S2, S4, S5 and S3 and the ORFS reading frame which codes for S4 is superposed on those which code for S2 and S3 (FIG. 3). On the basis of these results it is possible to conclude that the sequences determined contain the genes which code for the subunits of the pertussis toxin, and hence the open reading frames will be termed genes below.

In accordance with the present invention a transcription signal, very similar to the concensus sequence for the *E. coli* promotors, was identified before the gene which codes for S1.

In fact a region—10, TAAAAT, which contains five of the six base pairs of the concensus sequence is associated with a region—35, TGCTGACC, which contains six of the eight bases of the concensus sequence—35.

The distance between the two regions—35 and —10 is 21 base pairs.

At the end 3' of the gene which codes for S3 there has been identified an inverted repeated sequence followed by a poly-T sequence which could represent a termination site.

Since no other promoter before the four genes S2, S3, S4 and S5 has been identified in the DNA fragment it may be deduced that these genes are organized in a single operon and are transcribed as a single polycistronic mRNA.

The presence of a single Shine-Dalgarno sequence located nine base-pairs before the ATG of the gene S1, strongly suggests that this is the ribosomal binding site which enables the translation of the S1 mRNA.

The presence of a new consensus sequence, TCC (T) GG, located eight to twelve base pairs before each ATG initiation codon for the four genes, suggests that this site is responsible for the translation of the entire mRNA.

Moreover it was found that the gene S4, which is produced in stoichiometric quantities of 2 to 1 with respect to the other genes, is the only one which is preceded by a slightly modified consensus sequence, TCCTG, which probably increases the translation efficiency.

A characteristic common to all the subunits of the pertussis toxin is the presence, in the gene, of a sequence immediately preceding the mature protein, which codes for a 27–42 amino acid peptide the characteristics of which are typical of signal peptides involved in the secretion of the proteins.

This suggests that the various subunits are synthesized as proproteins, processed and secreted individually in the periplasmic space and subsequently processed, assembled and released into the extra-cellular space in the form of a single protein.

It has also been found that the signal peptide for S4 is unexpectedly long (42 amino acids) and has the highest aminoterminal positive charged described until now.

Since the positively-charged aminoterminal regions play an important role in the efficiency of production of the secreted proteins, the unusual structure of the signal peptide for S4 could cause increased translation of the gene S4.

It was also noted that, in the absence of the subunit S3 as occurs in the mutant BP356, the pertussis toxin is not excreted into the culture medium. Consequently, this protein is necessary for the complete assembly of the pertussis toxin.

The cloned DNA fragment or further fragments thereof, the said fragments containing at least one gene which codes for at least one subunit of the pertussis toxin, must be capable of being inserted in an expression vector and the hybrid plasmid thus obtained may be used to transform a micro-organism.

The transformed micro-organisms, grown in a suitable culture medium, are able to express the DNA fragment or fragments thereof by synthesis of the pertussis toxin or one or more subunits of the pertussis toxin.

Cloning vectors suitable for the purpose may be selected from natural plasmids known in the art or synthetic vectors obtained by recombinant DNA techniques.

In particular, the plasmid of *E. coli* pEMBL8 with about 4000 base pairs is used, this containing the gene for resistance to ampicillin and restriction sites useful for the cloning, such as: HindIII, pstI, AccI, HincII, SalI, BamHi, AvaI, SmaI, Xmai, EcoRI (Dente L. et al (Nucleic Acids Research 11, 1645–1655 (1983)), and the plasmids 31A, 31B and 31C derived from the vector PEX29 (Klinert M. et al. Inf. Imm. 49, 329–335 (1985)) which contain the gene which codes for the DNA polymerase of the phage MS2 placed under the control of the inducible promoter pL and a polylinker inserted before the end of the gene of the MS2 polymerase in three possible frames, so as to be able to break each possible DNA fragment in the same frame of the MS2 poymerase.

Examples of micro-organisms used as host cells are strains of *Escherichia coli, Bacillus subtilis,* Saccharomyces, or eucaryotic cells.

In accordance with the present invention, there are used cells of *E. coli* JM 101 (New England Biolabs 32 Tozer Road, Beverly, Mass. 01915-9990 USA) and cells of *E. coli* K-12 H1trp (described by Remant E. Gene 15: 81–93 (1981)) which produce a heat-sensitive repressor which, at 30°, completely inhibits the transcription of the gene of the MS2 polymerase preventing the production of proteins fused to it and, at 42° C., is inactivated giving good production of the polymerase and of the proteins fused to it.

The choice of the cloning vector and of the micro-organism to be transformed are not however limited by the present invention.

In accordance with the present invention, the 4696 base-pair fragment of chromosomal DNA obtained as described above, was inserted in the plasmid vector of *E. coli* pEMBL-8 after digestion of the plasmid DNA with the restriction enzyme Eco RI.

The hybrid plasmid obtained, designated pPT101, was then used to transform cells of *E. coli* JM101 (New England Biolabs) made competent by the method described by Cohen S. et al. (Proc. Natl. Acad. Sci. U.S. 69, 2110 (1972)).

The strain of *E. coli* (pPt101) was deposited in the American Type Culture Collection on Jun. 8, 1985 with the number ATCC 67854 as a substitute for ATCC 53212.

In order to check the ability of the transformed micro-organism to express the cloned DNA, fragment, the *E. coli* strain (pPT101) was cultivated in a suitable culture medium.

More particularly, the strain was grown in LB medium (DIFCO) at a temperature of 37° C. up to an absorbance of 0.75, measured in the culture broth at 590 nm.

The cells were then subjected to lysis and the pertussis toxin was determined directly in the cellular lysate by immunoenzymatic methods.

The biological activity of the pertussis toxin was determined by the method reported by Hewlett E. L. et al. (1983) (Infect. Immun. 40, 1198–1203), the change in form of the CHO cells incubated with the cellular lysate under examination being analysed.

The results obtained confirm that the 4696 base-pair fragment of *Bordetella pertussis* chromosomal DNA contains the genes which code for the five subunits of the pertussis toxin and the said toxin can be neutralized by antibodies against the toxin itself.

According to one embodiment of the present invention, the genes which code for the individual subunits of PT were cloned in the plasmids 31A, 31B, 31C derived from the vector PEX29 and the hybrid plasmids thus obtained and designated PTE255 (S1), PTE211 (S2), PTE221 (S3), PTE240 (S4) and PTE230 (S5) were used to transform cells of *E. coli* K-12 H1 trp.

The cells thus transformed were then cultivated in a suitable culture medium and the subunits, obtained as fused proteins, were recovered, purified and tested to determine their biological activities.

The results obtained show that all five subunits, when injected into rabbits, induce the formation of specific antibodies.

Moreover, the fused S1 protein shows the same enzymatic activity as the entire PT toxin, thus showing not only an immunological but also a functional identity with the natural S1.

In fact ADP-ribosylation tests carried out by incubating fused S1 with homogenized ox retina (ROS) in the presence of NAD marked with $^{32}P$, indicate that the subunit S1 binds the ADP-ribose group to the transducine present in the retina.

Hence both the pertussis toxin and the individual subunits obtained by the method of the present invention may be used for the preparation of vaccines against pertussis and diagnostic kits for determining specific antibodies in clinical samples from individuals infected with pertussis.

Analysis of the sequences given in the present invention also shows a certain similarity between the amino acid sequence in the subunit S1 of the pertussis toxin and that of the subunit A of the cholera toxin (J. Mekalanos et al. Nature 306, 551–557, 1983) (FIG. 7).

There is thus a possibility of preparing a vaccine capable of neutralizing cholera and pertussis simultaneously, with the use of the peptide S1 made by chemical synthesis or by recombinant DNA techniques.

The toxin in column A was treated with a reducing agent before being applied to the gel.

The toxin in column B was not reduced.

S2 and S3, although having the same deduced molecular weight (table 1—data from literature), had different mobilities on SDS-PAGE.

S5 was slightly coloured and also, having a lower molecular weight than that of S4 (table 1—data from the literature), under reducing conditions migrated more slowly than S4.

FIG. 2: Aminoterminal sequence of the subunits S1, S2, S3 and S4 determined by means of a micro-sequencer in the gaseous phase with the use of the individual subunits purified as in FIG. 1.

A=alanine; C=cysteine, D=aspartic acid; E=glutamic acid; F=phenylalanine; G=glycine; H=histidine; I=isoleucine; K=lysine; L=leucine; M=methionine; N=asparagine; P=proline; Q=glutamine; R=arginine; S=serine; T=threonine; V=valine; W=tryptophan; Y=tyrosine; X=unidentified amino acid residue.

All the sequences given are exactly in accordance with the nucleotide sequences with the single exception of the glutamine-2 in S2 which was found to be a threonine (FIG. 3).

FIGS. 3(A and B): Nucleotide sequence of the Eco RI fragment containing the five genes which code for the pertussis toxin.

The amino acid sequence of the five subunits of the pertussis toxin deduced from the nucleotide sequence is also given.

The arrows, before the amino acid sequences, indicate the start of the mature subunits as identified by comparison with the aminoterminal sequences in FIG. 2.

In the case of S5, the arrow indicates the expected start of the mature subunit.

Before the sequence of each subunit, the amino acid sequence of the expected peptide signals is given.

Upstream of the gene which codes for S1 are indicated the expected promoter and Shine-Dalgarno sequences.

The sequences TCC (T) GG are present before S2, S3, S4 and S5.

At the end of the gene which codes for S3 the arrows above the nucleotide sequence indicate an inverted repetitive sequence followed by a poly-T sequence (underlined) which represents a possible transcription termination site.

Four open reading frames (ORFS) having the same use as the codons of the genes of the pertussis toxin are indicated by dotted lines.

Figure 3B:
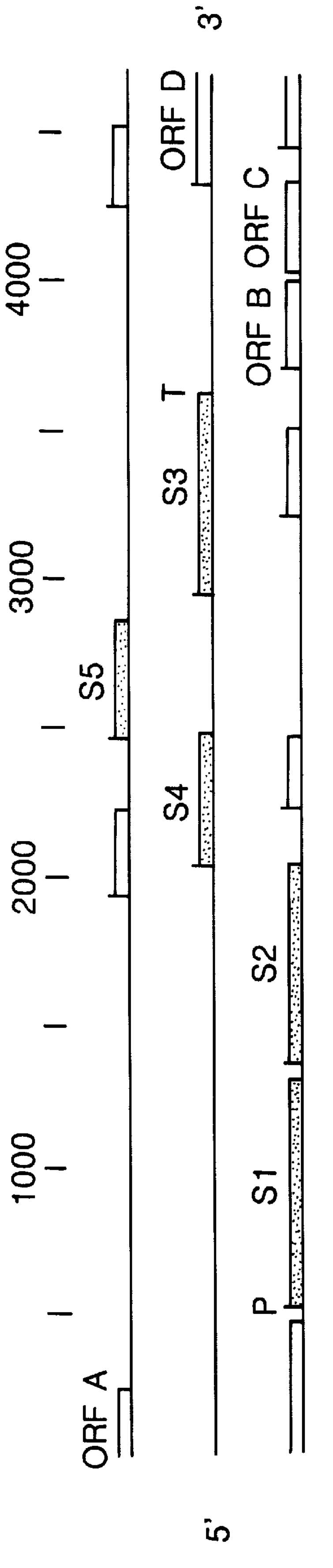

FIG. 3B: Schematic representation of the ORFS frames in the sequence given in FIG. 3A.

The frames 1, 2 and 3 are shown from top to bottom and only the open reading frames with at least 200 base pairs are given.

P: expected promoter sequence

T: expected terminator sequence

FIG. 4: Amino acid sequence of the signal peptides of the five subunits of the pertussis toxin.

The sequence (S) (P) A×A precedes the site at which cutting occurs.

Figure 5A:
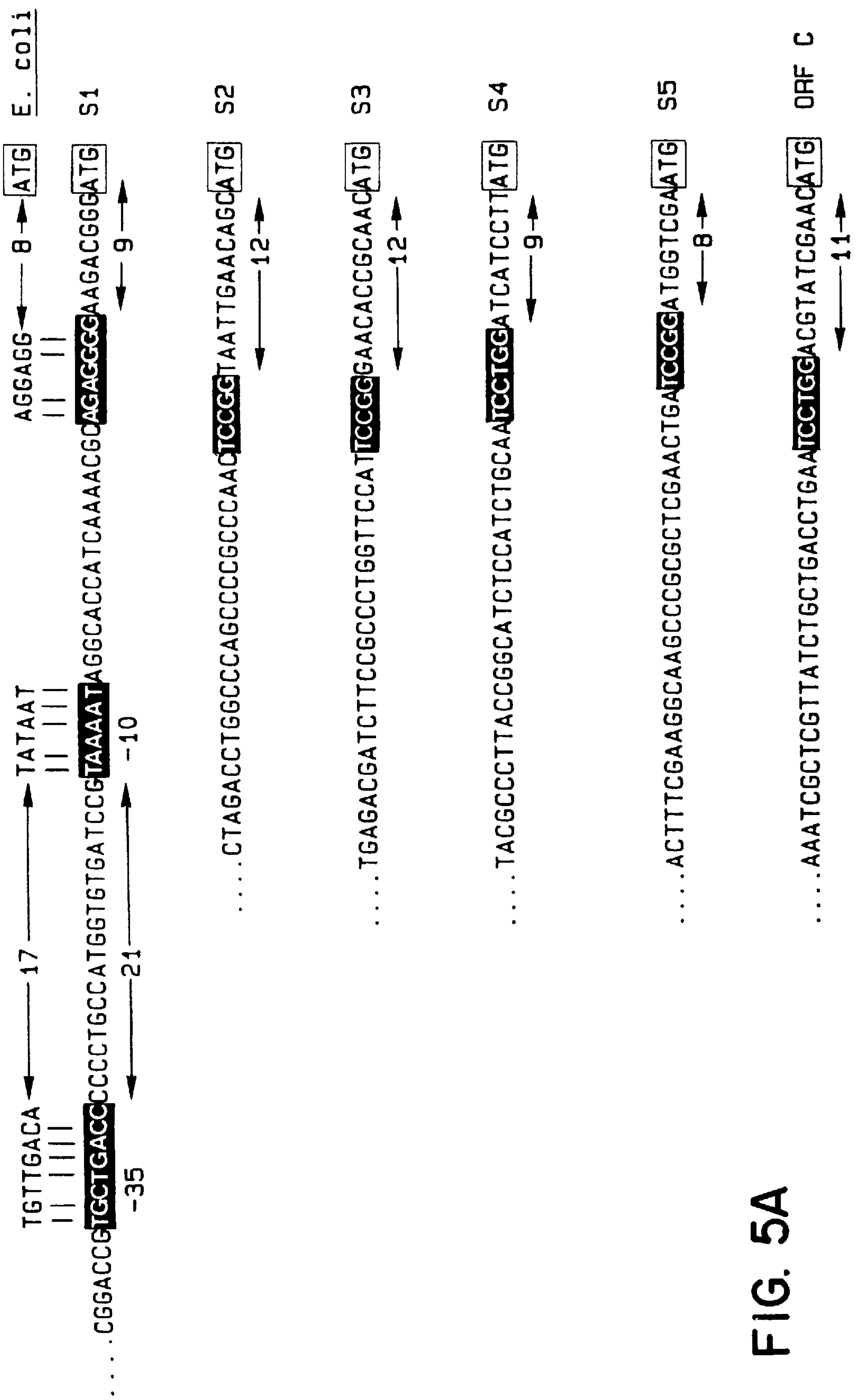

FIGS. 5(A and B): Translation and transcription signals. The initiation ATGs of the codons of the various ORFS are aligned and shown to the right.

Upstream of the ATG of S1 are shown the expected promoter and Shine Dalgarno sequences.

The respective sequences of *E. coli* are given above.

Upstream of the ATG of the other ORFS is given the sequence TCC (T) GG.

This sequence was not identified before the other ATG codone present in the entire nucleotide sequence given in FIG. 3.

FIG. 5B: This gives the structure of the expected termination sequence.

FIG. 6: This shows the correspondence between the amino acid sequences of S2 and S3. The arrows indicate the sites at which the preproteins are cut and the start of the matured subunits.

Figure 7:
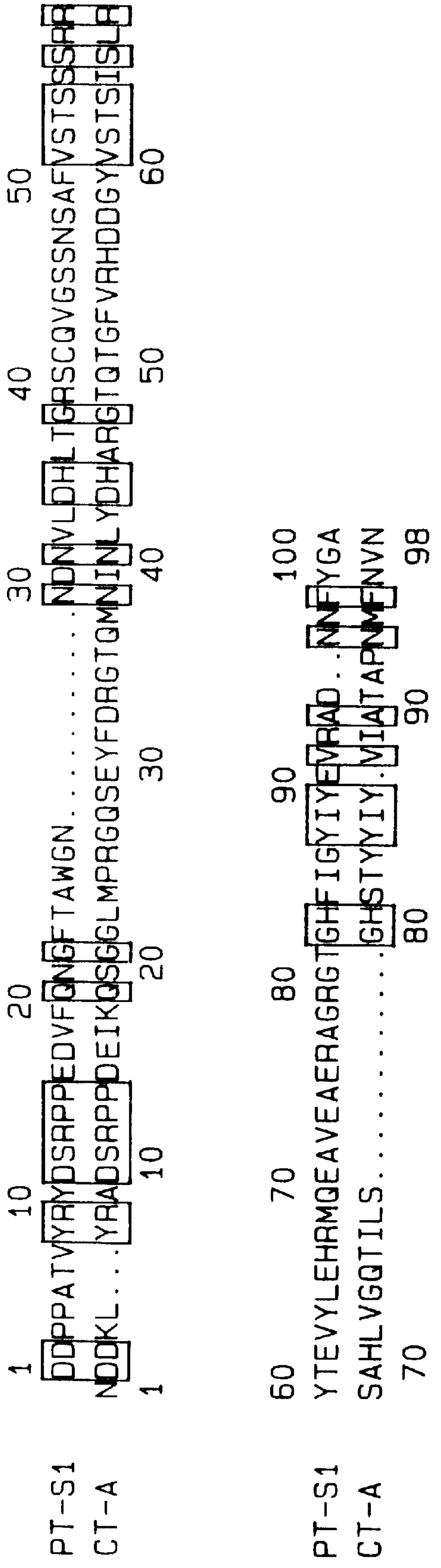

FIG. 7: Comparison of the amino acid sequence of the subunit S1 of the pertussis toxin and the subunit A of the cholera toxin. The corresponding amino acids in the two proteins are bracketed.

Figure 8:
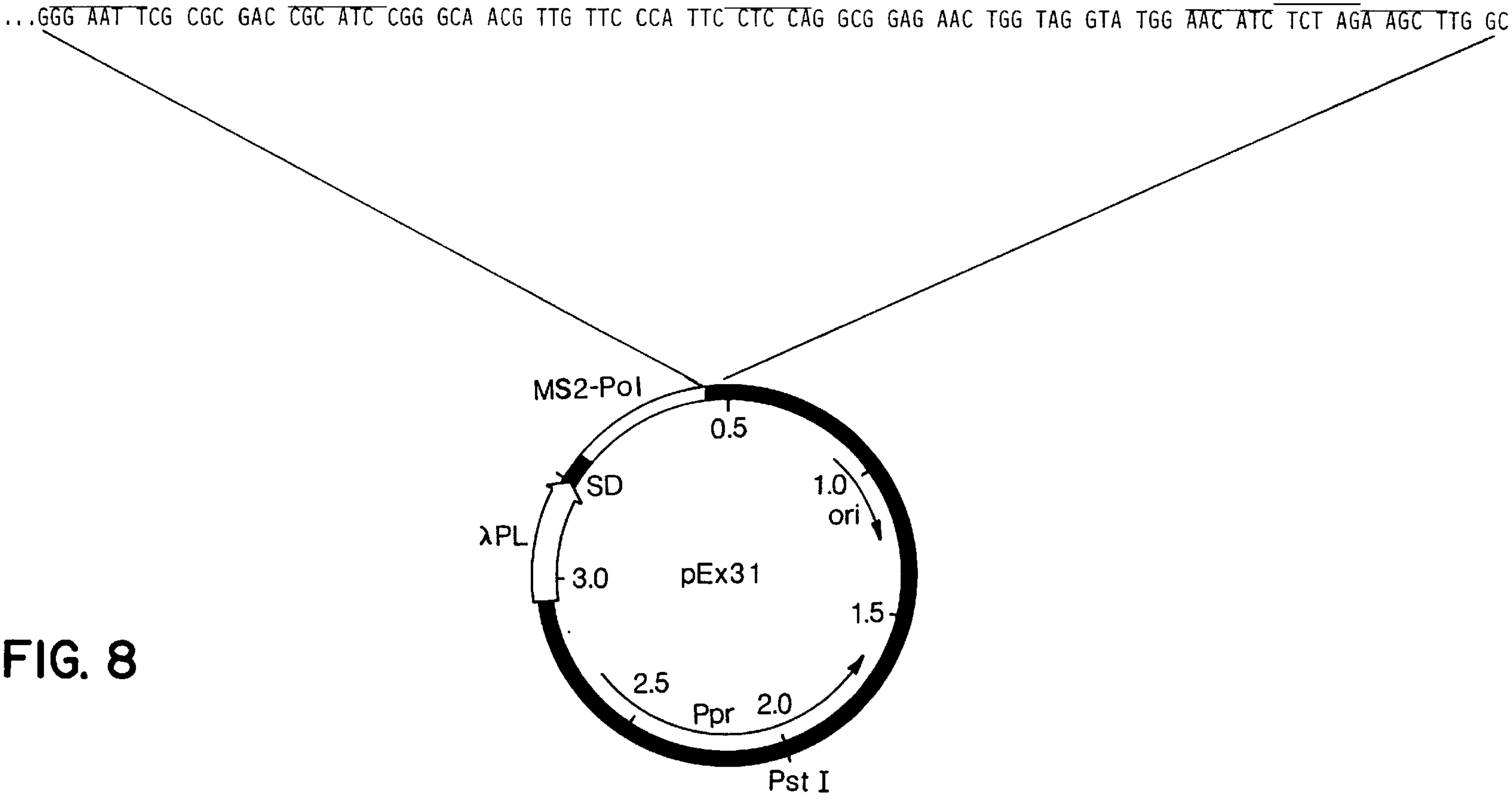

FIG. 8: The three plasmids 31A, 31B, and 31C and the introduction of the polylinker into the three possible frames are shown.

FIG. 9: This shows the cloning scheme for the genes which code for the five subunits of the pertussis toxin in the plasmids 31A, 31B and 31C and the construction of the hybrid plasmids PTE255 (S1), PTE211 (S2), PTE221 (S3), PTE240 (S4) and PTE230 (S5).

Figure 10A:
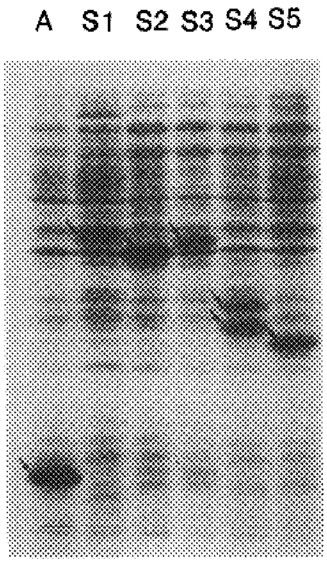

FIGS. 10(A–C):

FIG. 10A: This shows the electrophoresis of the total lysate of the strains which produce the polymerase of MS2 and the five subunits fused thereto (S1–S5).

Figure 10B:
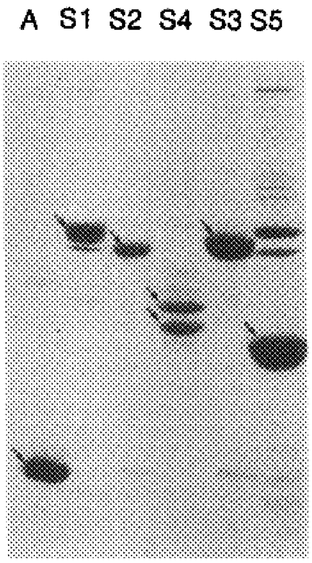

FIG. 10B: Electrophoresis of the partially-purified, fused proteins (S1, S2, S3, S4 and S5) on 15% acrylamide gel.

Figure 10C:
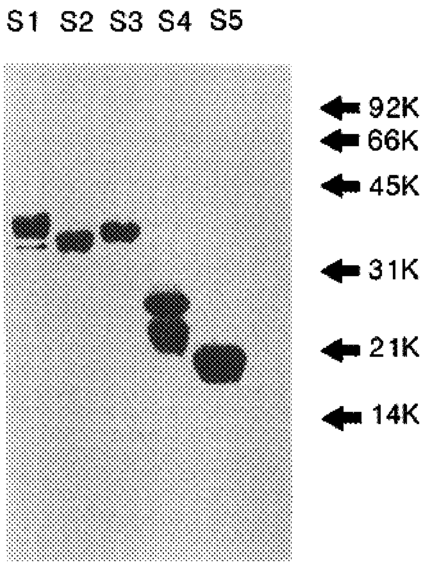

FIG. 10C: Electrophoresis of the purified fused proteins (S1, S2, S3, S4, S5) on 15% acrylamide gel.

Figure 11:
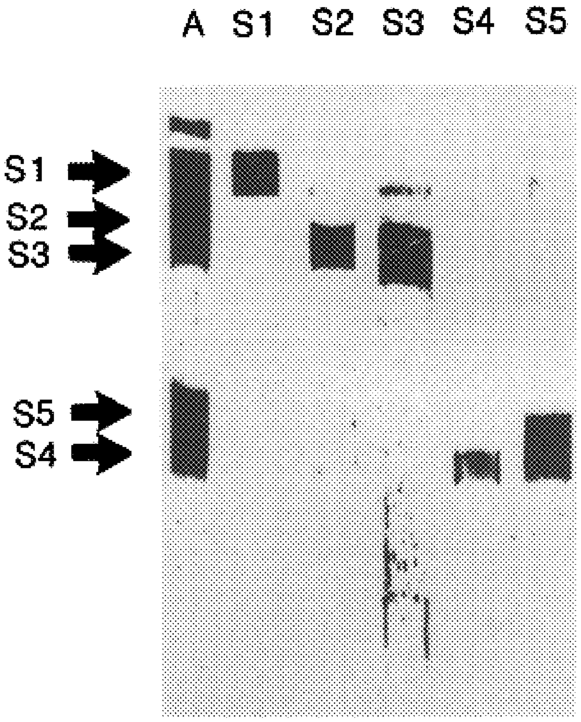
Figure 12:
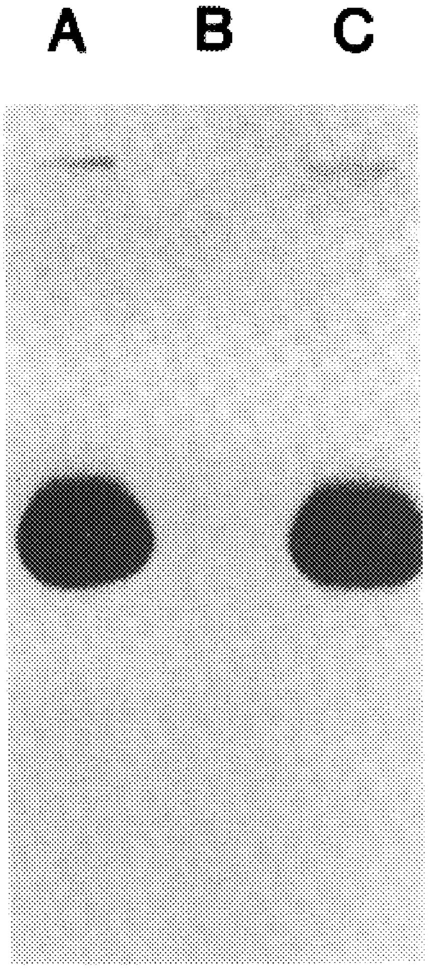

FIGS. 11(A–F) shows:

A): Western blot of the pertussis toxin incubated with goat serum against the entire toxin; this serum reacts with all five subunits:

B): Western blot of PT incubated with anti-fused S1 anti-serum: only the subunit S1 detected;

C): Western blot of PT incubated with anti-fused S2 anti-serum: only the subunit S2 detected;

D): Western blot of PT incubated with anti-fused S3 anti-serum: only the subunit S3 detected;

E): Western blot of PT incubated with anti-fused S4 anti-serum: only the subunit S4 detected;

F): Western blot of PT incubated with anti-fused S5 anti-serum: only the subunit S5 detected;

FIG. 12 Autoradiography on polyacrylamide gel indicating enzymatic activity of: lane A, pertussis toxin; lane B, the absence of pertussis toxin results in no mark; and lane C, fused S1.

FIG. 13: Nucleotide sequence of the DNA region which contains genes of the pertussis toxin. The sequence at the center is that of *Bordetella pertussis* while above and below respectively are given the difference found in the sequences of *B. bronchiseptica* and *B. parapertussis.*

Figure 14:
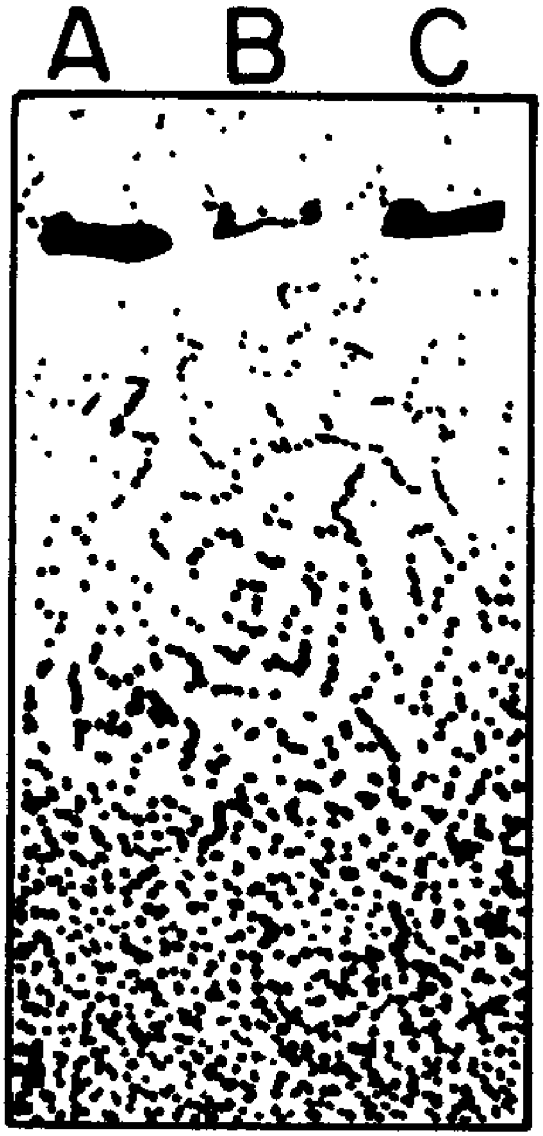

FIG. 14: Southern blot showing that *Bordetella pertussis* (lane A) may be distinguished from *B. parapertussis* (lane B) and bronchiseptica (lane C) by the magnitude of the Eco RI fragment which hybridizes with the clone pPT101.

FIG. 15: Amino acid sequence of the five subunits of the pertussis toxin. The sequence at the center is that of *Bordetella pertussis* while above and below respectively are given the differences found in *B. bronchiseptica* and *B. parapertussis.*

Figure 16:
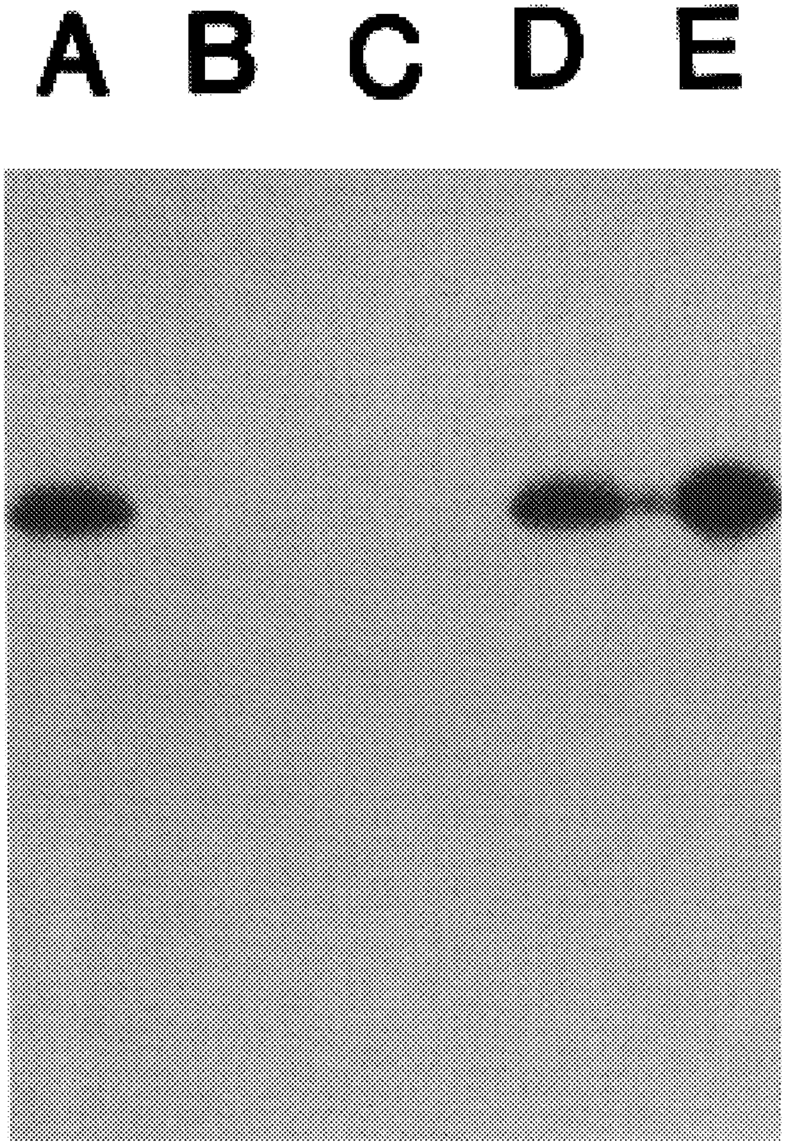

FIGS. 16(A–E): Enzymatic activity of the subunit S1 produced in *E. coli* as the fusion protein.

A: S1 of *B. pertussis*

B: MS2 polymerase from the vector pEX31a

C: Subunit S3

D: S1 of *B. parapertussis*

E: S1 of *B. bronchiseptica*

TABLE 1: Comparison of the amino acid composition in percentages, molecular weights and total charges of the five subunits of the pertussis toxin. A: experimental data given by Tamura et al. (Biochem. 21, 5516–5522 (1982)).

B: Data deduced from the nucleotide sequence.

TABLE 1

| | S1 | | S2 | | S3 | | S4 | | S5 | |
|---|---|---|---|---|---|---|---|---|---|---|
| | A | B | A | B | A | B | A | B | A | B |
| Ala | 10.6 | 11.5 | 6.5 | 6.0 | 11.7 | 11.0 | 9.4 | 8.1 | 9.8 | 8.0 |
| Arg | 5.9 | 9.3 | 6.2 | 6.0 | 6.1 | 6.5 | 5.1 | 5.4 | 3.3 | 3.0 |
| Asp + Asn | 9.3 | 9.4 | 6.3 | 6.5 | 6.3 | 6.0 | 5.3 | 4.5 | 8.2 | 8.1 |
| Cys | 1.0 | 0.8 | 1.3 | 3.0 | 1.1 | 3.0 | 0.9 | 3.6 | 1.6 | 4.0 |
| Gly | 11.2 | 7.2 | 13.0 | 10.5 | 11.9 | 10.0 | 9.6 | 6.3 | 8.7 | 8.0 |
| Glu + Gln | 10.6 | 10.2 | 8.7 | 7.5 | 9.0 | 8.0 | 9.5 | 8.2 | 9.3 | 9.1 |
| His | 1.7 | 2.1 | 2.4 | 2.0 | 1.0 | 1.0 | 0.5 | 0.9 | 3.0 | 3.0 |
| Ile | 3.2 | 3.8 | 4.2 | 5.5 | 5.0 | 6.5 | 2.0 | 1.8 | 3.4 | 3.0 |
| Leu | 5.5 | 3.4 | 7.3 | 7.5 | 8.1 | 8.0 | 8.4 | 9.0 | 13.8 | 15.1 |
| Lys | 2.2 | 0.0 | 3.4 | 3.0 | 2.7 | 2.5 | 6.9 | 7.3 | 4.7 | 5.0 |
| Met | 1.6 | 2.1 | 1.5 | 1.5 | 1.1 | 1.5 | 5.1 | 7.2 | 1.6 | 2.0 |
| Phe | 3.5 | 3.0 | 3.2 | 2.5 | 3.2 | 2.5 | 3.6 | 4.5 | 4.9 | 5.0 |
| Pro | 4.4 | 3.8 | 4.6 | 4.5 | 5.7 | 5.0 | 9.1 | 10.0 | 5.6 | 5.0 |
| Ser | 10.6 | 9.4 | 8.5 | 8.5 | 6.3 | 5.0 | 8.0 | 5.4 | 6.9 | 6.0 |
| Thr | 7.4 | 7.2 | 10.4 | 10.0 | 8.2 | 8.0 | 5.0 | 4.5 | 6.9 | 7.0 |
| Trp | — | 0.8 | — | 1.0 | — | 0.5 | — | 0.0 | — | 1.0 |
| Tyr | 4.6 | 8.0 | 7.6 | 8.0 | 7.9 | 9.5 | 2.2 | 1.8 | 4.3 | 4.0 |
| Val | 6.7 | 7.6 | 4.9 | 6.0 | 4.7 | 5.0 | 9.4 | 10.9 | 4.0 | 3.0 |
| MW[a] | 28.0 | 26.22 | 23.0 | 21.92 | 22.0 | 21.86 | 11.7 | 12.06 | 9.3 | 10.94 |
| pI: charge[b] | 5.8 | −4.0 | 8.5 | +2.0 | 8.8 | +3.0 | 10.0 | +5.0 | 5.0 | −3.0 |

a) Molecular weight in kilodaltons b) In order to compare the entire charge of the subunits, we have given the experimental isoelectric point at A and the nett charge calculated for each subunit at B.

The nett charge is calculated as ((Lys+Arg)−(Glu+Asp)).

The experimental examples which follow are illustrative and non-limiting of the invention.

EXAMPLE 1

Determination Of The Aminoterminal Sequence Of The Subunits Of The Pertussis Toxin A strain of *B. pertussis* BP165 was grown in a fermentor (Palias System N.B. App. Fabr. Van door De Bilt), provided with an agitator, with a capacity of 50 l, containing 40 l of Verwey culture medium with the following composition:

| | | |
|---|---|---|
| Bacto casamino acids (DIFCO) | g. | 14 |
| KCl | " | 0.2 |
| $K_2PO_4$ | " | 0.5 |
| $MgCl_2.6H_2O$ | " | 0.1 |
| nicotinic acid | " | 0.02 |
| glutotathione | " | 0.01 |
| Starch | " | 1.00 |
| $H_2O$ | | 1 liter |
| pH 6.8 | | |

previously sterilised at 120° C. for 15 minutes, under aeration, at a temperature of 36.5° C. for 28 hours.

At the end of the said period of time, the cells were separated from the culture broth by centrifuging and the pertussis toxin was recovered from the supernatant liquor by affinity chromotography on Affi-Gel blue (100–200 mesh) by BioRAd and on fetuin-sepharose as described by Sejura R. D. et al. [The J. Biol. Chem. 258, 23, 14647–14651 (1983)].

The protein obtained had a purity of more than 95%.

Figure 1:
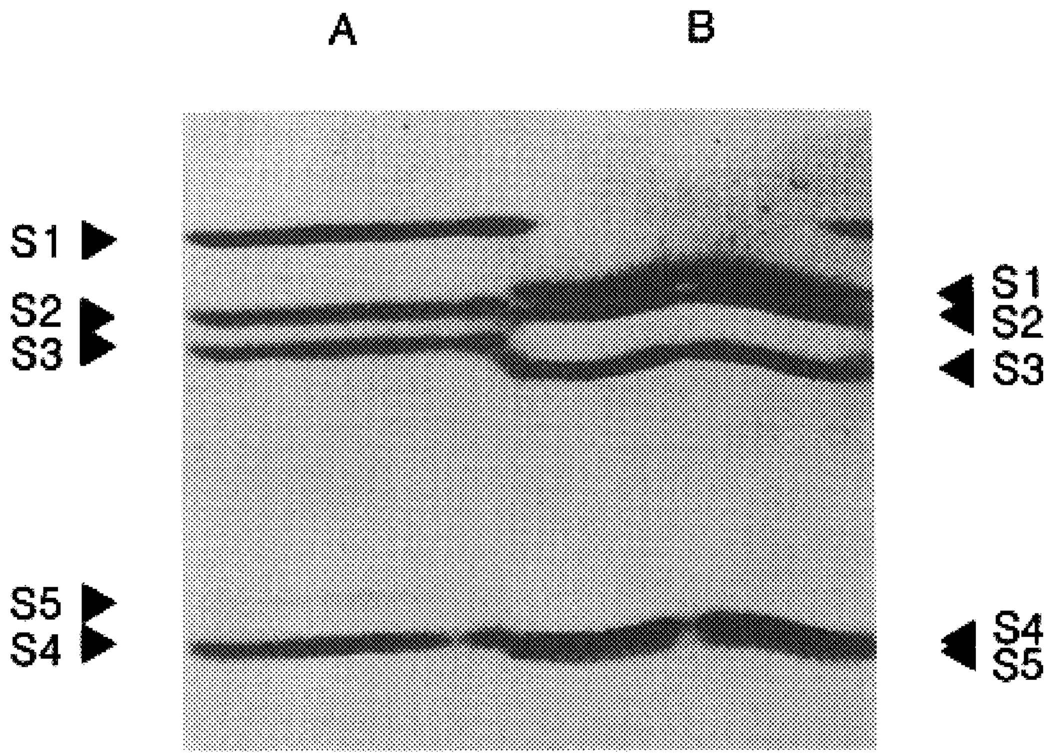
FIG. 1: Electrophoresis of the pertussis toxin purified by affinity chromotography on 15% polyacrylamide (PAGE)—sodium dodecylsulphate (SDS) gel.

The protein was then subjected to electrophoresis on a 15% (p/p) polyacrylamide gel containing sodium dodecylsulphate (SDS) at 125 volts for 5 hours and the five subunits were separated, as given in FIG. 1.

Each of these bands was cut and subjected to electroelution by the method of Hunkapiller M. W. et al [Methods in Enzymology 91, 227–236 (1983)].

Thus the five purified subunits were obtained.

The aminoterminal sequence of each of the subunits obtained was determined subsequently with the use of a gaseous-phase micro-sequencer model 470A (Applied Biosystems, Foster City, Calif.-USA) in accordance with the operating instructions.

FIG. 2 shows the aminoterminal sequence of the subunits S1, S2, S3 and S4.

EXAMPLE 2

Cloning Of The DNA Fragment Containing The Genes Which Code For The Five Subunits Of The Pertussis Toxin The strain *B. pertussis* BP 356 is a mutant strain containing a transposon (TN5) inserted in the chromosome.

The strain, described by Weiss A. A. et al. in Infect. Immun. 42, 33–41 (1983), was produced by Stanley Falkow, Stanford University.

A culture of *B. pertussis* BP 356 in the exponential phase (100 ml of Verwey medium) was centrifuged and the cells resuspended in 2 ml of 25% sucrose, 50 mM Tris, 1 mM EDTA (pH8).

To the suspension were then added 50 μl of lysozyme (40 mg/ml) and, after 5 minutes, 10 μl of proteinase K (20 mg/ml).

To the agitated suspension were added 0.4 ml of EDTA (0.05 M).

The cells were subjected to lysis by the addition of 0.25 ml of Sarkosil (10%) at 0° C. to the cell suspension.

The lysated cells were then suspended in 35 ml of a solution containing 69.6 g of CsCl in 55.2 ml of buffer, 50 mM Tris, 1 mM EDTA (pH8) containing 50 μg of phenyl methyl sulphonylfluoride, an inhibitor for the proteinase K. The solution was then centrifuged at 50,000 revolutions per minute (rpm) for 16 hours in a 70 t i Beckmann SOV t i and the chromosomal DNA thus separated was then recovered as a viscous band. 500 μg of chromosomal DNA thus obtained were dialyzed against 100 ml of distilled water to remove the CsCl and then partially digested with five units (U) of restriction enzyme Sau 3 A1 (Boehringer) in 5 ml of 50 mM NaCl, 10 mM Tris, 10 mM $MgSO_4$, 1 mM dithiothreitol buffer (pH7.4).

The digested DNA was precipitated by the addition to the solution of 12 ml of ethanol and, after separation, was resuspended in 0.5 ml of 10 mM Tris, 1 mM EDTA buffer.

This volume was loaded on to a 10% to 40% gradient of sucrose dissolved in 35 ml of 1 mM NaCl, 10 mM Tris, 1 mM EDTA buffer (pH 7.5).

The gradient was then centrifuged at 26000 rpm for 16 hours in a Beckman SW 28 rotor.

After this, 1 ml fractions were collected and the molecular weight of the DNA content of each fraction was determined by electrophoresis in agarose, as reported by Maniatis T. et al. "Molecular Cloning a Laboratory Manual", Cold Sprig Harbor N.Y. (1982).

The fractions containing the DNA fragments with 15000–20000 base pairs (bp) were then dialyzed and the DNA precipitated with ethanol as described above.

The precipitated DNA was separated by centrifuging and resuspended in 100 μl of 10 mM Tris, 1 mM EDTA buffer (pH 7.5) to a final concentration of 1 μg/ml of DNA.

The chromosomal DNA fragments were then cloned.

This was carried out with the use of an *E. coli* lambda phage vector EMBL 4 prepared as described by Frishauf A. et al. J. Mol. Biol. 170, 827–842 (1983).

1 μg of DNA of the phage vector EMBL 4, previously cut with two U of restriction enzyme Bam HI, and 1 μl of the solution containing the fragments of DNA with 15000–20000 bp were mixed in 5 μl of 1 mM ATP, 20 mM Tris, 10 mM $MgCl_2$, 10 mM dithiothreitol buffer (pH 7.6) in the presence of one U of T4 DNA ligase.

The ligase reaction was carried out at a temperature of 15° C. for 16 hours.

At the end of this period, the recombinant DNA obtained was inserted in lambda phages without DNA, with the use of the Packagene Kit of Promega Biotec (Maniatis T. et al. Molecular Cloning a Laboratory Manual Cold Spring Harbor N.Y. (1982)).

The recombinant phages thus obtained were used to transform the strain *E. coli* strain NM 539 (Promega Biotec.)

The transformed cells of *E. coli* NM 539 were plated on LB medium (Bacto Triptone 10 g, Bacto Y. E. 5 g, NaCl 10 g, $H_2O$ 1 liter pH 7.5) giving about 30000 plates of recombinent phages.

About 5000 recombinant phages were hybridized by hybridization on a plate with a radioactive probe for the TN5 DNA, in order to identify those phages containing the DNA fragment in which the transposon TN5 was inserted.

Twelve recombinant phages were positive on hybridization. The DNA was then extracted from these phages by the extraction methods given above.

1 μg of recombinant phage DNA was cut with two U of the restriction enzyme Eco RI in 20 μl of 50 mM Tris, 100 mM NaCl, 10 mM $MgSO_4$ buffer (pH 7.4), the solution being kept at a temperature of 37° C. for one hour.

The digested solution of DNA was then loaded on to a 1% agarose gel and subjected to electrophoresis for two hours at 120 volts for six hours.

The fragments of recombinant phage DNA thus separated were transferred on to nitrocellulose and hybridized with a radioactive probe for TN5 DNA in order to identify the Eco RI fragment containing the transposon TN5.

In this manner a positive Eco RI fragment of about 10500 bp was isolated which contained the entire sequence of TN5 flanked on one side by about 1100 bp and on the other by about 3500 bp of chromosomal DNA of *B. pertussis* BP 356.

1 μg of the Eco RI fragment was cut with two U of the enzyme Hinc II in 25 μl of 50 mM NaCl, 10 mM Tris, 10 mM $MgSO_4$4, 1 mM dithiothreitol buffer (pH 7.4), at 37° C. for 1 hour).

At the end of this period, the solution containing the digested DNA fragments was subjected to electrophoresis on 1% agarose gel for six hours at 120 volts, transferred onto nitrocellulose and then hybridized with the radioactive probe for TN5 DNA, in order to identify the fragments containing the junction between the TN5 and the chromosomal DNA.

Thus two fragments were identified, one with about 500 bp and the other with about 1900 bp.

The two fragments were then purified by electroelution and cloned in the phage vectors M13 mp8 and m13 mp9 (New England) the DNA of which had previously been cut with the restriction enzyme Hinc II.

The nucleotide sequence of the two fragments was then determined starting from the Hinc II site with the use of the technique described by Sanger F. S. (Proc. Natl. Acad. Sci. 74, 5463 (1977)).

At about 400 nucleotides from the HincII site of the larger fragment (1900 bp), the nucleotide sequence given in FIG. 3A—from 3030 to 3100 bp was identified and, translated into the corresponding amino acids, gave the amino acid sequence determined by us for the subunit S3 as described in Example 1 and given in FIG. 2.

This result indicates that in the strain *B. pertussis* 356, the TN5 is inserted in the gene which codes for the subunit S3 of the PT and confirms that the fragment of DNA cloned by us contains the gene for the pertussis toxin.

The fragment thus identified was then used as a hybridization probe to identify the gene for the PT present in the chromosomal DNA of *B. pertussis* BP165.

A gene library was again constructed for this strain in the phage vector EMBL 4, in the same manner as described for *B. pertussis* BP 356.

At the end of the cloning operation, an Eco RI fragment was isolated with 4696 bp which we knew contained at least the gene which codes for the subunit S3 in that it hybridized with the specific probe S3.

In order to check whether this fragment also contained the genes which code for the other PT subunits, the fragment, or parts of it, were cloned in the phage vectors M13 mp8 and M13 mp9 and then the nucleotide sequence of the entire fragment was determined.

Analysis of the nucleotide sequence of the entire fragment, given in FIG. 3, shows that this fragment also contains the genes which code for the subunits S1, S2 and S4, in that the translation of the nucleotide sequence of the DNA fragment in the corresponding amino acid sequence corresponds to the amino acid sequences determined by us for the subunits S1, S2 and S4 and given in FIG. 2.

Once the beginning of the amino acid sequence had been identified from the data given in FIG. 2, it was possible to deduce the entire amino acid sequence of the said subunits.

The analysis of the chemical and physical properties of the various subunits deduced from the amino acid sequence, such as the molecular weight, amino acid composition and electric charge, are in accordance with the data in the literature(Tamura et al. (1982) Biochemistry 21, 5516–5522).

It was also noted that a common characteristic of all five subunits was the presence in the gene of a sequence immediately before the mature protein which coded for a peptide with 27–42 amino acids and which had characteristics typical of the peptides involved in the secretion of the proteins, that is the presence of one or more positive charges on the terminal amino group followed by a hydrophobic zone (FIG. 4).

This shows that the subunits were produced in the form of preproteins and these were subsequently processed during secretion.

All the secretion signals also terminated with the sequence (S) (P)A×A which is typical of other secretion signals.

Among the genes which code for S4 and S3 was also identified a nucleotide sequence, from 2461 to 2862 bp, which codes for a peptide which has the same properties as the other secretion signals and terminates with the sequence SPADVA, followed by an amino acid sequence which has exactly the same amino acid composition as that given in the literature for the subunit S5 (Table 1).

This has enabled us to establish that the Eco RI fragment with 4696 bp cloned by us also contains the gene for the subunit S5 and hence has enabled us to determine the amino acid sequence of the latter (FIG. 3).

Further analysis of the nucleotide sequence of the DNA. fragments isolated and cloned by us has enabled the location of a promoter in the zone 440 bp to 485 bp, which has the same characteristics as those of *E. coli*, and of a termination sequence in the zone 3608 to 3670 bp.

This means that the five genes of the pertussis toxin are organised in a typical bacterial operon and are transcribed in a single mRNA.

EXAMPLE 3

Construction of the Hybrid Plasmid pPT 101 Containing the Genes Which Code for the Pertussis Toxin 1 μg of plasmid DNA of *E. coli* pEMBL-8 described by Dente L. (1983) Nucl. Acids Res. 11, 1645–1655 containing the gene which gives resistance to ampicillin were cut with two U of Eco RI enzyme in 20 μl of 100 mM NaCl, 50 mM Tris, 10 mM MgSO 4 buffer (pH 7.4) at 37° C. for one hour.

At the end of the digestion reaction, 3 μg of the Eco-RI DNA fragment with 4696 bp, the sequence of which is given in FIG. 3, were added to the solution containing the cut plasmid DNA and reacted in the presence of one U of T4 DNA ligase (BRL) under the conditions recommended by the manufacturer.

The ligase mixture was then used to transform cells of ampicillin-sensitive *E. coli* JM 101 (New England Biolabs) rendered competent.

The transformed cells were selected on LB plates containing 100 μl/ml of ampicillin in order to isolate those cells which contain the hybrid plasmid.

Among the clones of ampicillin-resistant (AmpR) *E. coli* thus obtained, it was possible to isolate clones containing the hybrid plasmid pEMBL 8 containing the DNA fragment which codes for PT by the technique of hybridization with a probe for the sequence of the PT gene.

One of these hybrid plasmids was designated pPT 101 by us.

The *E. coli* JM 101 strain containing the plasmid has been deposited by us at the American Type culture Collection under ATCC-62854 as a substitute for ATCC-53212.

EXAMPLE 4

Construction of the Hybrid Plasmid PTE 253 Containing the Gene Which Codes for the Subunit S1

The construction of the hybrid plasmid was carried out in the manner given in example 3 above, by ligating the plasmid 31B, previously digested with the restriction enzymes Bam HI and Xba I, with the Sau3al-Xba from 612 to 1317 of the 4696 bp fragment corresponding to the gene which codes for S1.

The ligase mixture was then used to transform cells of competent *E. coli*, the transformed calls being selected on LB plates (DIFCO) containing ampicillin.

The hybrid plasmid PTE 235 (S1) was separated from one of the positive clones and its sequence is given in FIG. 9 where the lower case letters indicate the coding sequence for the polymerase MS 2 and the upper case letters indicate the sequence which codes for S1.

The resulting protein contains all the subunit S1 apart the first amino acid Asp.

EXAMPLE 5

Construction of the Hybrid Plasmid PTE 211 Containing the Gene Which Codes for the Subunit S2

This was carried out as in Example 3 above with the use of the plasmid 31A digested with Bam HI and treated with DNA polymerase to fill the cohesive termini and the Sau96-SmaI fragment from 1433 to 2064 of the 4696 bp fragment, corresponding to the gene which codes for S2, was treated with DNA polymerase (Klenow) to fill the cohesive termini.

The hybrid plasmid PTE 211 (S2) isolated from one of the positive transformants had the sequence given in FIG. 9.

The resulting fused protein contained the sequences of the polymerase of MS2 (lower case letters to the left) fused to an amino acid of the peptide leader of the subunit S2 (upper case letters), and hence to the protein S2 (lower case letters to the right).

EXAMPLE 6

Construction of the Hybrid Plasmid PTE 221 Containing the Gene Which Codes for the Subunit S3

This was carried out as in Exam-pie 3 above with the use of the plasmid 31C digested with Bam HI and treated with DNA polymerase to fill the cohesive termini and the SphI-DdeI fragment from 3014 to 3628 of the 4696 bp fragment, corresponding to the gene which codes for S3, was treated with DNA polymerase to eliminate the cohesive termini.

The hybrid plasmid PTE 221 (S3) isolated from one of the positive transformants had the sequence given in FIG. 9.

The fused protein which resulted from it contained the polymerase MS2 (lower case letters to the left) fused to five amino acids of the peptide leader of the subunit S3 (upper case letters), and hence to the natural subunit S3 (lower case letters to the right).

EXAMPLE 7

Construction of the Hybrid Plasmid PTE 240 Containing the Gene Which Codes for the Subunit S4

This was carried out as in example 3 above, with the use of the plasmid 31B cut with Bam HI and treated with polymerase and the BstN1-BstN1 fragment from 2151 to 2600 of the 4696 bp fragment corresponding to the gene which codes for S4.

The sequence of the hybrid plasmid PTE 240 (S4) thus obtained is given in FIG. 9.

The fused protein which results from it contains the polymerase of MS2 (lower case letters) fused to two amino acids of the peptide leader of the subunit S4 (upper case letters), and hence to the natural subunit S4.

EXAMPLE 8

Construction of the Hybrid Plasmid PTE 230 Containing the Gene Which Codes for the Subunit S5

This was carried out as in Example 3 above, with the use of the plasmid 31A cut by Bam HI and treated with DNA polymerase to fill the cohesive termini and the Aat2-SnaBI fragment from 2558 to 3210 of the 4696 bp fragment, corresponding to the gene which codes for S5.

The sequence of the hybrid plasmid PTE230 obtained is given in FIG. 9.

The resulting fused protein contained the polymerase of MS2 (lower case letters to the left), two amino acids of the peptide leader of the subunit S5 (upper case letters and hence the natural subunit S5 (lower case letters to the right).

EXAMPLE 9

Production of Pertussis Toxin and Experiment to Determine its Activity

The strain *E. coli* JM 101 (pPT 101) was grown in a 100 ml flask containing 10 ml of LB, under mild agitation, at a temperature of 37° C. for 16 hours.

0.1 ml of this culture was then used to inoculate 10 ml of LB medium and grown at 37° C. up to an absorbance $OD_{590}$ of 0.75.

The culture broth was then centrifuged at 4° C. and the cells thus separated were resuspended in 0.5 ml of 10 mM Tres (pH 7.5).

The cell suspension was subjected to lysis by ultrasonics in a Branson Sonifier-cell Disruptor 200 (Bransonsonic Power Co., a SmithKline Company).

The presence and biological activity of the pertussis toxin were then determined directly on the cellular lysate by means of CHO cells, by the method reported by Hewlett, E. L. et al. (1983) Infect. Immun. 40, 1198–1203. The CHO cells used were obtained in our laboratory by mutation of CHO ATCC CCL 61 cells. 10,000 CHO cells were incubated in 2.5 ml of medium (the composition of which is given by Hewlett E. L. et al. (1983) (Infect. Immun. 40, 1198–1203) in the presence of 5 μl of cell extract of *E. coli* JM 101 (pPT 101), 5 μl of *E. coli* JM 101 cells containing the unmodified plasmid PEMBL-8 and 0.1 ng of pertussis toxin as a standard.

Part of the cell extract had previously been incubated with a 1:100 dilution of ordinary goat antiserum (A) and another part with a 1:100 dilution of the same goat antiserum taken after immunisation with the pertussis toxin.

After 48 hours of incubation at 37° C. the results were read in the manner described by Hewlett in the text indicated above.

A value of 4 (+) was attributed to a form change of the CHO cells, a value of 1 (+) to a minimum form change and (−) to a lack of form change.

The results are given in table 2.

TABLE 2

Activity on CHO cells of the toxin produced by the recombinant clones

| Sample | Whole | Goat anti-toxin antibodies | Preimmune goat antiboidies |
|---|---|---|---|
| 0.1 ng Toxin | ++++ | — | ++++ |
| *E. coli* extract containing pPT101 ATCC 53212 now 67854 | +++ | — | +++ |
| *E. coli* extract containing PEMBL8 | — | — | — |

0.1 ng of the purified pertussis toxin was used as a positive control. The sample was constituted by 5 μl of *E. coli* lysate containing the plasmid PT101. The negative control was constituted by the same strain of *E. coli* containing the plasmid used as a vector, without the genes for the pertussis toxin (pEMBL8).

It may be seen from table 2 that the extract of cells of *E. coli* (pPT101) ATCCL 67854 as a substitute for ATCC 53212 gave a positive result and the toxin could be neutralized by anti-pertussis toxin antibodies but not by antibodies from the same goat before it had been immunized.

The strain *E. coli* JM 101 (pEMBL8) did not have any activity in this test.

We may thus conclude that the fragment of Eco RI chromosomal DNA with 4696 base pairs, cloned by us in the plasmid pEMBL8 is able to synthesize a toxin which is functionally identical to the pertussis toxin produced by *B. pertussis* BP163 and the pertussis toxin can be neutralised by antibodies for the toxin itself.

EXAMPLE 10

Expression and Purification of the 5 Subunits of the Pertussis Toxin a) Expression of the 5 subunits The hybrid plasmids PTE255 (S1), PTE211 S(2), PTE221 (S3), PTE240 (S4) and PTE230 (S5) constructed as described in the examples 4 to 8 were introduced by transformation of the strain of *E. coli*, K12 H1trp.

Each of tie transformed strains was then grown in 10 ml of LB medium at 30° C. for one night. At the end of this period, the 10 ml of each culture were added to 400 ml of fresh LB medium in two-liter flasks.

The flasks were kept under agitation at 30° C. for two hours and at a temperature of 42° C. for 2.5 hours.

The cultures were centrifuged and the cells separated and resuspended in 3 ml of 25% sucrose, 10 ml Tris—HCl (pH 8.0), 1 mM EDTA.

5 $\mu$l of each of the said cultures then had added to it 80 $\mu$l of lysis buffer (4% SDS, 125 mM Tris (pH 6.8), 10% B-mercaptoethanol, 10% glycerol and 0.02% bromophenol blue, they were brought to boiling point for five minutes and then loaded onto a 15% polyacrylamide gel.

The proteins were then subjected to electrophoresis at 25 milliamps for five hours and the gel coloured and decoloured as reported by Laemli (Nature, 227, 680–85, 1970).

FIG. 10A shows the electrophoresis of the total lysate of the strains which produce the polymerase of MS2 (A) and the 5 unpurified subunits (S1–S5) fused to this.

b) Purification of the 5 subunits

The cells of each of the said cultures were resuspended in 3.2 ml of 2.5% sucrose solution, 0.1 ml of lysozyme (40 mg/ml) and 0.8 ml of 0.5M EDTA was added and they were incubated at 37° C. for 30 minutes.

At the end of this period, to each of the suspensions were added 8 ml of lysis buffer (1% Triton X 100, 50 mM Tris pH 6.00, 63 mM EDTA) and then they were kept at 0° C. for 15 minutes and at 37° C. for 30 minutes.

Subsequently the cells were subjected to sonic disruption and centrifuged at 10000 revolutions for 10 minutes.

The precipitate thus separated was resuspended in 5 ml of 1M urea, kept at 37° C. for 30 minutes, centrifuged and, after separation of the supernatant liquor, resuspended in 5 ml of 7M urea. Thus partial purification of the subunits produced was obtained as given in FIG. 10B.

The partially-purified proteins were resuspended again in 5 ml of 7M urea, loaded on to a preparative polyacrylamide gel (3 mm×50 cm) and subjected to electrophoresis at 50 milliamps for 8 hours.

After colourating, the band containing the fusion protein was cut and electroeluted at 200 volts for 48 hours in a dialysis bag.

The electroeluted protein was then dialysed against distilled water and precipitated by the addition of 9 volumes of acetone.

The protein was then recovered by centrifuging and resuspended in 0.1M $NaHCO_3$.

FIG. 10C shows the results obtained for the individual purified proteins.

Preparation of Sera Against the 5 Subunits

The purified, fused proteins (S1, S2, S3, S4 and S5) obtained as indicated in Example 10 above were used to immunized rabbits in accordance with the following scheme:

Day 1: 1 ml of solution containing about 1 mg of the fused protein was mixed with 1 ml of whole Freund adjuvant and injected subcutaneously into a rabbit.

Day 18: The treatment of Day 1 was repeated with the use of incomplete adjuvant.

Day 27: 1 ml of a solution with a protein content of about 1 mg was injected intravenously.

Day 37: The rabbits were bled and the serum recovered.

The anti-sera to the 5 subunits thus prepared were then tested by the Western Blot technique to check whether they recognized the five natural proteins.

About 100 mg of the purified pertussis toxin indicated in Example 1 was loaded on to a 15% polyacrylamide gel and subjected to electrophoresis.

The thus separated were then transferred on to nitrocellulose by electro-blotting.

The sheet of nitrocellulose containing the subunits was cut vertically into a number of identical strips each of which was subsequently analyzed by the Western blot technique.

In practice, the strips of nitrocellulose were suspended in PBS 0.15 M NaCl, 10 mM phosphates pH 7.4 containing 1 X Denhart(0.03% bovine albumin, 0.02% FiColl 70 and 0.02% poly-vinyl pyrrolidone) and 0.05% Tween for two hours and were washed two times, for 3 minutes each time, with PBS containing 0.05% of Tween 20.

They were subsequently incubated for one night at ambient temperature with a 1/100 dilution of the desired serum in PBS with the addition of 0.05% Tween 20.

They were then washed three times for 15 minutes each time, with a solution of 10 mM Tris, 0.9% NaCl and 0.1% Tween 20 (TES), incubated with a conjugate of gamma-globulin anti-globulin of goat-peroxidase or globular anti-globulin of rabbit peroxidase (Miles) diluted 1/100 in TBS and finally washed 3 times in TBS and once in Tris 0.01 M (pH 6.8) for 10 minutes. To each of the solutions was then added the substrate for the peroxides 20 ml Tris 0.05M pH 6.8, 5 ml 0.3% 4-chloro 1 naphthol in methanol and 7 $\mu$l of $H_2O_2$.

The reaction was stopped by washing the filters in distilled water.

The results given in FIG. 11 show that the fused proteins obtained with the use of the genes which code for the five subunits of PT, when injected into rabbits, induce the cremation of specific antibodies capable of recognizing each of the subunits of the natural toxin.

EXAMPLE 12

Analysis of the Enzymatic Activity of the Fused Protein S1

10$\mu$l of fused protein S1 and 10 $\mu$l of PT preincubated with 25 nM of dithiothreitol at ambient temperature for 30 minutes were added to a solution containing 10 $\mu$l of homogenised ox retina (ROS), 80 $\mu$l of $H_2O$ 5 $\mu$l of Tris 2M (pH7.5), 1 $\mu$l of GATP 10 mM, 10 $\mu$l of GTP 10 mM, 10 $\mu$l of thymidine and 1 $\mu$l (1 $\mu$Ci) of $^{32}$P AND.

The mixture was kept at ambient temperature for 30 minutes, centrifuged, the supernatant was separated and the precipitate containing the ROS was dissolved in sodium codecylsulphate loading buffer, loaded on to 15% polyacrylamide gel and subjected to a potential difference of 125 volts for 5 hours.

At the end of this period, the gel was dried and subjected to autoradiography.

The results (FIG. 12) show that lane A, the pertussis toxin (PT) ADP ribosyles the transducin, lane B, in the absence of the pertussis toxin this is not marked and lane C, the fused electroeluted S1 has the same ADP ribosylazing activity as PT.

EXAMPLE 13

Cloning, Sequence and Expression of the genes of *Bordetella bronchisentica* and *Bordetella parapertussis*

Although *B. bronchiseptica* and *B. pertussis* do not produce active pertussis toxin, we have found that they contain the coding genes for this. By operating as described in Examples 2, 3 and 4, we have cloned and sequenced the genes of *Bordetella bronchiseptica* (ATCC 4617) and *Bordetella parapertussis* (ATCC 9305) which code for the five subunits of the pertussis toxin.

The nucleotide sequence obtained, given in FIG. 13, shows that there are small differences between the three strains. One of these lacks the Eco RI site at 4696 and hence the genes of *B. bronchiseptica* and *B. parapertussis* are contained in Eco RI fragments with 4935 bp instead of 4696. This difference in dimensions may be used as a diagnostic criterion for distinguishing *B. pertussis* from *B. parapertussis* and *B. bronchiseptica*, in the following manner: Bordetella chromosomal DNA was digested with Eco RI on an agarose gel, transferred on to nitrocellulose and hybridized by the techniques described for the plasmid PPT 101 and its fragments of cloned DNA.

The results of the autoradiography enable the *B. pertussis* to be distinguished from the *B. parapertussis* and bronchiseptica which hybridize in a higher molecular weight band (FIG. 14).

FIG. 15 gives the amino acid sequences deduced from the five subunits in the three species of Bordetella. As may be seen, there are several changes of amino acids. To check whether these changes alter the function and immonogenicity of the subunits, operating as described in Example 4, we have expressed the genes which code for the subunit S1 of *B. bronchiseptica* and parapertussis . The fused proteins obtained were immunogenically similar to those of *B. pertussis* and in fact were recognized in Western blot by antitoxin antibodies of pertussis.

Moreover, by operating as described in Example 12, we found that both the proteins had the same enzymatic activity as the subunit S1 of *B. pertussis* (FIG. 16). This example shows that the proteins with the sequence given in FIG. 15 although containing several variations, may be used as a vaccine against pertussis.

What is claimed is:

1. A cloned and sequenced Eco RI fragment of *Bordetella pertussis* chromosomal DNA with 4696 base pairs containing the genes which code for the five subunits of the pertussis toxin or fragments thereof, where the fragments contain at least one gene which codes for at least one subunit of the pertussis toxin, characterized by the sequence given in FIGS. 3 and 13.

2. Hybrid plasmid obtained by the union of an expression vector and the Eco R1 fragment or fragments thereof as defined in claim 1.

3. Hybrid plasmid pPT101 according to claim 2, in which the 4696 base-pair Eco RI fragment is inserted in the Eco RI restriction site of PEMBL8.

4. Hybrid plasmid PTE255 according to claim 2, in which the Sau3A-Xba fragment which codes for the subunit S1 is inserted in the Bam HI-Xba I site of the plasmid 31B.

5. Hybrid plasmid PIE211 according to claim 2, in which the Sau96-SmaI fragment which codes for the subunit S2 is inserted in the Bam HI site in the plasmid 31A.

6. Hybrid plasmid PTE221 according to claim 2, in which the Sphl-Ddel fragment which codes for the subunit S3 is inserted in the Bam HI site in the plasmid 31C.

7. Hybrid plasmid PTE240 according to claim 2, in which the BstNl-BstNl fragment which codes for the subunit S4 is inserted in the Bam HI site of the plasmid 31B.

8. Hybrid plasmid PTE230 according to in claim 2, which the Ast2-SnaBI fragment which codes for the subunit S5 is inserted in the site Bam HI of the plasmid 31A.

9. Hybrid plasmid according to claim 2, where the DNA fragment or fragments thereof are placed under the control of the regulating sequence, promoter or ribosome binding site, which regulate their expressions.

10. A micro-organism transformed by an hybrid plasmid as defined in claims 3 to 8.

11. The micro-organism *Escherichia coli* transformed in accordance with claim 4.

12. The microorganism *Escherichia coli* ATCC 67854.

13. A method for the cloning and sequencing of the chromosomal DNA fragment according to claim 1, including:

a) isolating and cloning, in an *E. coli* lambda phage EMBL4, fragments of chromosomal DNA with 15,000–20,000 base pairs, obtained by the digention of the chromosomal DNA of *Bordetella pertussis* BP 356, a mutant strain which does not produce the pertussis toxin, which contains a transposon TN5 in its own chromosomal DNA;

b) isolating a fragment of recombinant phage DNA which hybridises with a probe marked for TN5 DNA from the positive recombinant phage;

c) cutting the garment of recombinant phage DNA with the restriction enzyme Hinc II and isolating a fragment with 1900 bp containing a nucleotide sequence which codes for the subunit S3 by hybridization with a probe for TN5 DNA;

d) isolating and cloning in an *E. coli* lambda phage EMBL4 fragments of chromosomal DNA with 15,000–20,000 base pairs obtained by the digestion of the chromosomal DNA of *Bordetella pertussis* BP165;

e) isolating a fragment of recombinant phage DNA which hybridizes with a probe for S3 obtained at point c) from the positive recombinant phages;

f) cutting the recombinant phage DNA fragment with the restriction enzyme Eco RI and isolating an Eco RI fragment of chromosomal DNA with 4696 base pairs by hybridization with a probe for S3 DNA;

g) inserting the fragment obtained from step (f) into the plasmid vector pPEML8 in the Eco RI restriction site, determining the nucleotide sequence of the DNA fragment and identifying genes which code for the five subunits of the pertussis toxin.

14. A method for the preparation of the pertussis toxin or one or more of the subunits of the pertussis toxin which includes the growth of a transformed micro-organism as defined in claims 10 to 11 in a culture medium.

15. An isolated gene consisting essentially of DNA encoding pertussis toxin.

16. A recombinant DNA vector containing the gene of claim 15.

17. An *E. coli* containing the recombinant DNA vector of claim 16.

* * * * *